US010925976B2

(12) United States Patent
Totary-Jain et al.

(10) Patent No.: US 10,925,976 B2
(45) Date of Patent: Feb. 23, 2021

(54) SMOOTH MUSCLE SPECIFIC INHIBITION FOR ANTI-RESTENOTIC THERAPY

(71) Applicant: THE TRUSTEES OF COLUMBIA UNIVERSITY IN THE CITY OF NEW YORK, New York, NY (US)

(72) Inventors: Hana Totary-Jain, Wesley Chapel, FL (US); Andrew Robert Marks, Larchmonth, NY (US); Steven O. Marx, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/806,007

(22) Filed: Nov. 7, 2017

(65) Prior Publication Data
US 2018/0110879 A1 Apr. 26, 2018

Related U.S. Application Data

(62) Division of application No. 14/390,988, filed as application No. PCT/US2013/035327 on Apr. 4, 2013, now abandoned.

(60) Provisional application No. 61/727,003, filed on Nov. 15, 2012, provisional application No. 61/620,404, filed on Apr. 4, 2012.

(51) Int. Cl.
C12N 15/11 (2006.01)
A61K 48/00 (2006.01)
C12N 15/86 (2006.01)

(52) U.S. Cl.
CPC ........ A61K 48/0058 (2013.01); A61K 48/005 (2013.01); C12N 15/111 (2013.01); C12N 15/86 (2013.01); C12N 2310/141 (2013.01); C12N 2320/30 (2013.01); C12N 2710/10043 (2013.01); C12N 2799/022 (2013.01); C12N 2830/008 (2013.01)

(58) Field of Classification Search
CPC .................................................. A61K 48/0058
See application file for complete search history.

(56) References Cited

U.S. PATENT DOCUMENTS

| 5,139,941 | A | 8/1992 | Muzyczka et al. |
| 5,252,479 | A | 10/1993 | Srivastava |
| 5,328,470 | A | 7/1994 | Nabel et al. |
| 5,747,469 | A | 5/1998 | Roth et al. |
| 6,017,524 | A | 1/2000 | Roth et al. |
| 6,143,290 | A | 11/2000 | Zhang et al. |
| 6,235,311 | B1 * | 5/2001 | Ullah ............... A61K 9/209 424/470 |
| 6,410,010 | B1 | 6/2002 | Zhang et al. |
| 6,511,847 | B1 | 1/2003 | Zhang et al. |
| 7,232,806 | B2 | 6/2007 | Tuschl et al. |
| 8,398,968 | B2 | 3/2013 | Mayall |
| 8,404,653 | B2 | 3/2013 | Zsebo |
| 2004/0057937 | A1 | 3/2004 | Jahoda et al. |
| 2006/0105360 | A1 | 5/2006 | Croce et al. |
| 2009/0131354 | A1 | 5/2009 | Bader et al. |
| 2009/0137421 | A1 * | 5/2009 | Mo ............... C12N 15/111 506/10 |
| 2009/0326051 | A1 | 12/2009 | Corey et al. |
| 2010/0041737 | A1 | 2/2010 | Naldini et al. |
| 2011/0172293 | A1 | 7/2011 | Fish et al. |
| 2012/0128643 | A1 * | 5/2012 | Biffi ............... C12N 15/111 424/93.21 |

FOREIGN PATENT DOCUMENTS

| EP | 2318016 | 2/2010 |
| EP | 2104736 | 11/2011 |
| EP | 2310507 | 1/2014 |
| WO | WO 1993/024641 | 12/1993 |
| WO | WO 1994/013788 | 6/1994 |
| WO | WO 2001/032840 | 5/2001 |
| WO | WO 2007/100870 | 9/2007 |
| WO | WO 2008/073921 | 6/2008 |
| WO | WO 2010/005850 | 1/2010 |
| WO | WO 2010/019574 | 2/2010 |
| WO | WO 2010/125471 | 11/2010 |
| WO | WO 2011/064354 | 6/2011 |
| WO | WO 2012/017449 | 2/2012 |
| WO | WO 2013/152230 | 10/2013 |

OTHER PUBLICATIONS

Zhu et al. (Journal of Biological Chemistry. May 11, 2007; 282(19: 14328-14336). (Year: 2007).*
Budker et al (J Gene Med. 2000; 2:76-88). (Year: 2000).*
Alpert, J. S., et al., "The risk of stent thrombosis after coronary arterial stent implantation," The American Journal of Medicine, vol. 123, No. 6, pp. 479-480 (Jun. 2010).
Altaras, N. E., et al., "Production and Formulation of Adenovirus Vectors," Adv. Biochem. Eng./ Biotechnol., vol. 99, pp. 193-260 (2005).
Anderson, W. French, "Human gene therapy," Nature, vol. 392, Supp., pp. 25-30, 8 pages (Apr. 30, 1998).
Anderson, W. French, "Human Gene Therapy," Science, vol. 256, pp. 808-813, 8 pages (May 8, 1992).
Annoni, A., et al., "In vivo delivery of a microRNA-regulated transgene induces antigen-specific regulatory T cells and promotes immunologic tolerance," Blood, vol. 114, No. 25, pp. 5152-5161, (Dec. 10, 2009).

(Continued)

Primary Examiner — Scott Long
(74) Attorney, Agent, or Firm — Thomas|Horstemeyer LLP

(57) ABSTRACT

The present invention provides for the incorporation of target sequences of microRNAs into the 3'UTR region of a gene of interest in nucleic acid vectors. The invention also provides for an expression system comprising such vectors, a pharmaceutical composition comprising such vectors, as well as methods of treating or preventing cardiovascular disease by using such vectors.

15 Claims, 8 Drawing Sheets

Specification includes a Sequence Listing.

(56) References Cited

OTHER PUBLICATIONS

Aronson, D. and Edelman, E. R., "Revascularization for coronary artery disease in diabetes mellitus: angioplasty, stents and coronary artery bypass grafting," Reviews in Endocrine and Metabolic Disorders, vol. 11, pp. 75-86 (2010).
Bandyopadhyay, P. K. and Temin, H. M., "Expression of Complete Chicken Thymidine Kinase Gene Inserted in a Retrovirus Vector," Mol. Cell Biol., vol. 4, No. 4, pp. 749-754 (Apr. 1984).
Bandyopadhyay, S., et al., "Development of the human cancer microRNA network," Silence 1:6, pp. 1-14 (2010).
Bartel, David P., "MicroRNAs: genomics, biogenesis, mechanism, and function," Cell, vol. 116, pp. 281-297 (Jan. 23, 2004).
Bartel, David P., "MicroRNAs: target recognition and regulatory functions," Cell, vol. 136, pp. 215-233 (Jan. 23, 2009).
Berkner, K. L., "Development of Adenovirus Vectors for the Expression of Heterologous Genes," Biotechniques, vol. 6, No. 7, pp. 616-629, 12 pages (Jul./Aug. 1988).
Berkner, K. L., "Expression of Heterologous Sequences in Adenoviral Vectors," Current Topics in Microbiology and Immunology, vol. 158, pp. 39-66 (1992).
Boettger, T., et al., "Acquisition of the contractile phenotype by murine arterial smooth muscle cells depends on the Mir143/145 gene cluster," The Journal of Clinical Investigation, vol. 119, No. 9, pp. 2634-2647 (Sep. 2009).
Breakefield, X. O. and Geller, A. I., "Gene Transfer into the Nervous System," Mol. Neurobiol., vol. 1, No. 4, pp. 339-371 (1987).
Brower, Vicki, "Naked DNA vaccines comes of age," Nature Biotechnology, vol. 16, pp. 1304-1305 (Dec. 1998).
Brown et al (Nature Medicine. Apr. 23, 2006; 12(5): 585-591).
Brown, B. D. and Naldini, L., "Exploiting and antagonizing microRNA regulation for therapeutic and experimental applications," Nature Reviews Genetics, vol. 10, pp. 578-585 (Aug. 2009).
Brown, B. D., et al., "Endogenous microRNA can be broadly exploited to regulate transgene expression according to tissue, lineage and differentiation state," Nature Biotechnology, vol. 25, No. 12, pp. 1457-1467 (Dec. 2007).
Brown, B. D., et al., "Endogenous microRNA regulation suppresses transgene expression in hematopietic lineages and enables stable gene transfer in hematopoietic lineages," Nature Medicine, vol. 12, No. 5, pp. 585-591 (Apr. 23, 2006).
Brummelkamp, T. R., et al., "A system for stable expression of short interfering RNAs in mammalian cells," Science, vol. 296, No. 5567, pp. 550-553 (Apr. 19, 2002).
Buchschacher, G. L. and Panganiban, A. T., "Human Immunodeficiency Virus Vectors for Inducible Expression of Foreign Genes," J. Virol., vol. 66, No. 5, pp. 2731-2739 (May 1992).
Calin, G. A., et al., "Frequent deletions and down regulation of microRNA genes miR15 and miR16 at 13q14 in chronic lymphocytic leukemia," Proc. Natl. Acad. Sci. USA, vol. 99, No. 24, pp. 15524-15529 (Nov. 26, 2002).
Camenzind, E., et al., "Stent Thrombosis Late After Implantation of First-Generation Drug-Eluting Stents: A Cause for Concern," Circulation, vol. 115, pp. 1440-1455 (2007).
Campagnolo, L., et al., "EGFL7 is a chemoattractant for endothelial cells and is up-regulated in angiogenesis and arterial injury," American Journal of Pathology, vol. 167, No. 1, pp. 275-284 (Jul. 2005).
Cassese, S. and Kastrati, A., "New-Generation Drug-Eluting Stents for Patients With Myocardial Infarction," JAMA, vol. 308, No. 8, pp. 814-815 (Aug. 22/29, 2012).
Cawood, R., et al., "Use of tissue-specific micro RNA to control pathology of wild-type adenovirus without attenuation of its ability to kill cancer cells," PLoS Pathogens, vol. 5, No. 5, pp. 1-10 (2009).
Chen, S.-H., et al., "Gene Therapy for Brain Tumors: Regression of Experimental Gliomas by Adenovirus-mediated gene transfer in vivo," Proc. Natl. Acad. Sci. USA, vol. 91, pp. 3054-3057 (Apr. 1994).

Chen, X., et al., "Role of miR-143 targeting KRAS in colorectal tumorigenesis," Oncogene, vol. 28, pp. 1385-1392 (2009).
Cheng, Y., et al., "MicroRNA-145, a Novel Smooth Muscle Cell Phenotypic Marker and Modulator, Controls Vascular Neointimal Lesion Formation," Circulation Research, vol. 105, pp. 158-166 (2009) (with Supplemental material; 13 pages).
Ciccarelli, M., et al., "Endothelial alpha1-adrenoceptors regulate neo-angiogenesis," Br. J. Pharmacol., vol. 153, No. 5, pp. 936-946 (Mar. 2008).
Clape, C., et al., "miR-143 interferes with ERK5 signaling and abrogates prostate cancer progression in mice," PLoS ONE, vol. 4, No. 10, pp. 1-8 (Oct. 2009).
Clarke, M. and Bennett, M., "The Emerging Role of Vascular Smooth Muscle Cell Apoptosis in Atherosclerosis and Plaque Stability," Am. J. of Nephrol., vol. 26, pp. 531-535 (2006).
Cleveland, W. L., et al., "Routine Large Scale Production of Monoclonal Antibodies in a Protein Free Culture Medium," J. Immunol. Methods, vol. 56, No. 2, pp. 221-234 (1983).
Cordes, K. R., et al., "miR-145 and miR-143 Regulate Smooth Muscle Cell Fate and Plasticity," Nature, vol. 460, No. 7256, pp. 705-710, 7 pages (Aug. 6, 2009).
Costa, M. A. & Simon, D. I., "Molecular basis of restenosis and drug-eluting stents," Circulation, vol. 111, pp. 2257-2273 (2005).
Daubman, Susan, "MicroRNAs in angiogenesis and vascular smooth muscle cell function," Circulation Research, vol. 106, pp. 423-425 (2010).
Dornburg, R., "Reticuloendotheliosis viruses and derived vectors," Gene Therap., vol. 2, No. 5, pp. 301-310 (Jul. 1995).
Dzau, V. J., et al., "Gene therapy for cardiovascular disease," Trends in Biotechnology, vol. 11, pp. 205-210 (May 1993).
Eglitis, M. A. and Anderson, W. F., "Retroviral vectors for introduction of genes into mammalian cells," Biotechniques, vol. 6, No. 7, pp. 608-614, 8 pages (Jul./Aug. 1988).
Elia, L., et al., "The knockout of miR-143 and -145 alters smooth muscle cell maintenance and vascular homeostasis in mice: correlates with human disease," Cell Death and Differentiation, vol. 16, pp. 1590-1598 (2009).
Eliyahu, H., et al., "Polymers for DNA Delivery," Molecules, vol. 10, No. 1, pp. 34-64 (Jan. 31, 2005).
Fiers, W., et al., "Complete nucleotide sequences of SV40 DNA," Nature, vol. 273, pp. 113-120 (May 11, 1978).
Fink, D. J., et al., "In Vivo Expression of B-Galactosidase in Hippocampal Neurons by HSV-Mediated Gene Transfer," Hum. Gene Ther., vol. 3, No. 1, pp. 11-19 (1992).
Finn, A. V., et al., "Vascular responses to drug eluting stents: importance of delayed healing," Arterioscler Thromb. Vasc. Biol., vol. 27, No. 7, pp. 1500-1510 (2007).
Fish, J. E. & Srivastava, D., "MicroRNAs: Opening a New Vein in Angiogenesis Research," Sci. Signal, vol. 2, No. 52, pe1, 3 pages (Jul. 6, 2009).
Fisher, K. J., et al., "Transduction with Recombinant Adena-Associated Virus for Gene Therapy is Limited by Leading String Synthesis," J. Virol., vol. 70, No. 1, pp. 520-532, 17 pages (Jan. 1996).
Forrester, J. S., et al., "A paradigm for restenosis based on cell biology: clues for the development of new preventive therapies," JACC, vol. 17, No. 3, pp. 758-769 (Mar. 1, 1991).
Freese, A., et al., "HSV-1 Vector Mediated Neuronal Gene Delivery," Biochem. Pharmacol., vol. 40, No. 10, pp. 2189-2199 (1990).
Friedmann, Theodore, "Progress toward human gene therapy," Science, vol. 244, No. 4910, pp. 1275-1281 (Jun. 16, 1989).
Garg, S., et al., "Coronary stents: looking forward," J. Am. Coll. Cardiol., vol. 56, Suppl. 10, pp. S43-S78 (2010).
Garg, Scot and Serruys, P. W., "Drug-eluting stents: a reappraisal," Heart, vol. 96, No. 7, pp. 489-493 (Apr. 2010).
Gorziglia, M. and Kapikian, A. Z., "Expression of the OSU Rotavirus Outer Capsid Protein VP4 by an Adenovirus Recombinant," J. Virol., vol. 66, No. 7, pp. 4407-4412, 7 pages (Jul. 1992).
Götte, M., et al., "miR-145-dependent targeting of Junctional Adhesion Molecule A and modulation of fascin expression are associated with reduced breast cancer cell motility and invasiveness," Oncogene, vol. 29, pp. 6569-6580 (2010).

(56) References Cited

OTHER PUBLICATIONS

Hager, G. L., et al., "Protein dynamics in the nuclear compartment," Curr. Opin Genet. Dev., vol. 12, No. 2, pp. 137-141 (2002).
Hammond, Scott M., "MicroRNAs as oncogenes," Curr. Opin Genet. Dev., vol. 16, No. 1, pp. 4-9 (2006).
Harris, T. A., et al., "MicroRNA-126 regulates endothelial expression of vascular cell adhesion molecule 1," Proc. Natl. Acad. Sci. USA, vol. 105, No. 5, pp. 1516-1521 (Feb. 5, 2008).
Hayashi, S., et al., "The Stent Eluting Drugs Sirolimus and Paclitaxel Suppress Healing of the Endothelium by Induction of Autophagy," The American Journal of Pathology, vol. 175, No. 5, pp. 2226-2234 (Nov. 2009).
Helseth, E., et al., "Changes in the Transmembrane Region of the Human Immunodeficiency Virus Type 1 gp41 Envelope Glycoprotein Affect Membrane Fusion," J. Virol., vol. 64, No. 12, pp. 6314-6318 (Dec. 1990).
Heron, M., et al., "Deaths: Final Data for 2006," Natl. Vital Stat. Rep., vol. 57, No. 14, pp. 1-134, 136 (Apr. 17, 2009).
Herweijer, H. and Wolff, J. A., "Gene Therapy progress and prospects: Hydrodynamic gene delivery," Gene Ther., vol. 14, No. 2, pp. 99-107, 11 pages (Jan. 2007).
Hoffman, Allan S., "Hydrogels for biomedical applications," Adv. Drug Delivery Rev., vol. 64, Supplement, pp. 18-23 (Dec. 2012).
Hwang, H.-W. and Mendell, J. T., "MicroRNAs in cell proliferation, cell death, and tumorigenesis," Br. J. Cancer, vol. 94, No. 6, pp. 776-780 (2006).
Iaccarino, G., et al., "AKT participates in endothelial dysfunction in hypertension," Circulation, vol. 109, pp. 2587-2593 (2004).
Iaccarino, G., et al., "Targeting Gbeta gamma signaling in arterial vascular smooth muscle proliferation: a novel strategy to limit restenosis," Proc. Natl., Acad. Sci. USA, vol. 96, pp. 3945-3950 (Mar. 1999).
Iakovou, I., et al., "Incidence, Predictors, and Outcome of Thrombosis After Successful Implantation of Drug Eluting Stents" JAMA, vol. 293, No. 17, pp. 2126-2130 (May 4, 2005).
Indolfi, C., et al., "Inhibition of cellular ras prevents smooth muscle cell proliferation after vascular injury in vivo," Nat. Med., vol. 1, No. 6, pp. 541-545 (1995).
International Search Report and Written Opinion issued by the U.S. Patent and Trademark Office as International Searching Authority for International Application No. PCT/US2013/035327 dated Aug. 7, 2013 (13 pages).
Isaka, Y., et al., "Electroporation-mediated gene therapy," Expert. Opin. Drug Deliv., vol. 4, No. 5, pp. 561-571 (Sep. 2007).
Ishida, M. and Selaru, F. M., "miRNA-Based Therapeutic Strategies," Curr. Anesthesiol. Rep., vol. 1, No. 1, pp. 63-70, 14 pages (Mar. 1, 2013).
Jager, L. and Ehrhardt, A., "Emerging Adenoviral Vectors for Stable Correction of Genetic Disorders," Curr. Gene Ther., vol. 7, No. 4, pp. 272-283 (Aug. 2007).
Jensen, Thomas G., "Cutaneous gene therapy," Ann. Med., vol. 39, No. 2, pp. 108-115 (2007).
Johnson, P. A., et al., "Effects of gene transfer into cultured CNS neurons with a replication-defective herpes simplex virus type 1 vector," Mol. Brain Res., vol. 12, No. 1-3, pp. 95-102 (Jan. 1992).
Joner, M., et al., "Pathology of drug-eluting stents in humans: delayed healing and late thrombotic risk," J. Am. Coll. Cardiol., vol. 48, No. 1, pp. 193-202 (2006).
Jukema, J. W., et al., "Restenosis after PCI: Part 1: pathophysiology and risk factors," Nat. Rev. Cardiol., vol. 9, pp. 53-62 (Jan. 2012).
Kalos, M., et al., "T Cells with Chimeric Antigen Receptors Have Potent Antitumor Effects and Can Establish Memory in Patients with Advanced Leukemia," Sci. Transl. Med., vol. 3, No. 95, pp. 1-21 (Aug. 10, 2011).
Kaneda T., et al., "Statins Inhibited erythropoietin-induced proliferation of rat vascular smooth muscle cells," European Journal of Pharmacology, 36 pages (Aug. 25, 2010).
Kelly, E. J., et al., "Engineering microRNA responsiveness to decrease virus pathogenicity," Nature Medicine, vol. 14, No. 11, pp. 1278-1283 (Nov. 2008).

Kikuchi, Y., et al., "Cutaneous gene delivery," J. Dermatol. Sci., vol. 50, No. 2, pp. 87-98 (May 2008).
Kim, Michael S. and Dean, L. S., "In-Stent Restenosis," Cardiovascular Therapeutics, vol. 29, pp. 190-198 (2011).
Korshunov, V. A. and Berk, B. C., "Smooth muscle apoptosis and vascular remodeling," Current Opinion in Hematology, vol. 15, No. 3, pp. 250-254 (2008).
Kotani, J., et al., "Incomplete Neointimal Coverage of Sirolimus Eluting Stents," Journal of the American College of Cardiology, vol. 47, No. 10, pp. 2108-2111 (2006).
Landgraf, P., et al., "A Mammalian microRNA Expression Atlas Based on Small RNA Library Sequencing," Cell, vol. 129, pp. 1401-1414 (Jun. 29, 2007).
Lee, K. Y., et al., "Controlled degradation of hydrogels using multifunctional cross linking molecules," Biomaterials, vol. 25, No. 13, pp. 2461-2466 (Jun. 2004).
Lee, N. S., et al., "Expression of small interfering RNAs targeted against HIV-1 rev transcripts in human cells," Nat. Biotechnol., vol. 20, No. 5, pp. 500-505 (May 2002).
Liu, H. T., et al., "Rapamycin Inhibits Re-Endothelialization after Percutaneous Coronary Intervention by Impeding the Proliferation and Migration of Endothelial Cells and Inducing Apoptosis of Endothelial Progenitor Cells," Tex. Heart Inst. J., vol. 37, No. 2, pp. 194-201 (2010).
Ma, X., et al., "Drug-eluting stents," Int. J. Clin. Exp. Med., vol. 3, No. 3, pp. 192-201 (2010).
Madzak, C., et al., "Efficient in vivo encapsidation of a shuttle vector into pseudo-simian virus 40 virions using a shuttle virus as helper," J. Gen. Virol., vol. 73, Part 6, pp. 1533-1536 (1992).
Malek, N. P., et al., "A mouse knock-in model exposes sequential proteolytic pathways that regulate p27Kip1 in G1 and S phase," Nature, vol. 413, No. 6853, pp. 323-327 (Sep. 20, 2001).
Mann, R. and Baltimore, D., "Varying the Position of a Retrovirus Packaging Sequence Results in the Encapsidation of Both Unspliced and Spliced RNAs," J. Virol., vol. 54, No. 2, pp. 401-407 (May 1985).
Margolskee, R. F., "Epstein-Barr Virus Based Expression Vectors," Curr. Top Microbial. Immunol vol. 158, pp. 67-95 (1992).
Marks, Andrew R., "Sirolimus for the prevention of in-stent restenosis in a coronary artery," N. Engl. J. Med., vol. 349, No. 14, pp. 1307-1309 (Oct. 2, 2003).
Marx, S. O. & Marks, A. R., "Bench to bedside: the development of rapamycin and its application to stent restenosis," Circulation, vol. 104, pp. 852-855, 10 pages (Aug. 21, 2001).
Marx, S. O., et al., "Rapamycin-FKBP inhibits cell cycle regulators of proliferation in vascular smooth muscle cells," Circulation Research, vol. 76, pp. 412-417, 16 pages (Mar. 1, 1995).
Marx, S. O., et al., "Vascular smooth muscle cell proliferation in restenosis," Circ. Cardiovasc. Interv., vol. 4, No. 1, pp. 104-111, 16 pages (Feb. 2011).
Matsuo, Y., et al., "K-Ras Promotes Angiogenesis Mediated by Immortalized Human Pancreatic Epithelial Cells Through Mitogen-Activated Protein Kinase Signaling Pathways," Mol. Cancer Res., vol. 7, No. 6, pp. 799-808 (Jun. 2009).
Mendell, J. T., "MicroRNAs Critical Regulators of Development, Cellular Physiology and Malignancy," Cell Cycle, vol. 4, No. 9, pp. 1179-1184 (Sep. 2005).
Miller, A. D., et al., "Deletion of the gag Region from FBR Murine Osteosarcoma Virus Does Not Affect Its Enhanced Transforming Activity," J. Virol., vol. 55, No. 3, pp. 521-526 (Sep. 1985).
Miller, A. D., et al., "Design of Retrovirus Vectors for Transfer and Expression of the Human B-Globin Gene," J. Virol., vol. 62, No. 11, pp. 4337-4345 (Nov. 1988).
Miller, A. Dusty, "Human gene therapy comes of age," Nature, vol. 357, No. 6378, pp. 455-460, 6 pages (Jun. 11, 1992).
Miller, A. Dusty, "Retrovirus packaging cells," Hum. Gene Therap., vol. 1, No. 1, pp. 5-14 (Spring 1990).
Miller, C. L., et al., "An Activation-Dependent, T Lymphocyte Specific Transcriptional Activator in the Mouse Mammary Tumor Virus env Gene," Mol. Cell Biol., vol. 12, No. 7, pp. 3262-3272 (Jul. 1992).

(56) References Cited

OTHER PUBLICATIONS

Miyagishi, M., et al., "U6 promoter-driven siRNAs with four uridine 3' overhangs efficiently suppress targeted gene expression in mammalian cells," Nat. Biotechnol., vol. 20, No. 5, pp. 497-500 (May 2002).
Moses, J. W., et al., "Sirolimus-Eluting Stents versus Standard Stents in Patients with Stenosis in a Native Coronary Artery," The New England Journal of Medicine, vol. 349, No. 14, pp. 1315-1323 (Oct. 2, 2003).
Moss, Bernard, "Vaccinia and other poxvirus expression vectors," Curr. Opin. Biotechnol., vol. 3, No. 5, pp. 518-522 (1992).
Muzyczka, N., "Use of adeno-associated virus as a general transduction vector for mammalian cells," Curr. Top Microbial. Immunol., vol. 158, pp. 97-129 (1992).
Nordmann, A. J., et al., "Mortality in randomized controlled trials comparing drug-eluting vs. bare metal stents in coronary artery disease: a meta-analysis," European Heart Journal, vol. 27, pp. 2784-2814 (2006).
Ohi, S., et al., "Construction and replication of an adeno-associated virus expression vector that contains human B-globin cDNA," Gene, vol. 89, No. 2, pp. 279-282 (1990).
Orlandi, A. and Bennett, M., "Progenitor cell-derived smooth muscle cells in vascular disease," Biochemical Pharmacology, vol. 79, pp. 1706-1713 (2010).
Osada, H. and Takahashi, T., "MicroRNAs in biological processes and carcinogenesis," Carcinogenesis, vol. 28, No. 1, pp. 2-12 (2007).
Owens, G. K., et al., "Molecular Regulation of Vascular Smooth Muscle Cell Differentiation in Development and Disease," Physiol. Rev., vol. 84, pp. 767-801 (2004).
Paddison, P. J., et al., "Short hairpin RNAs (shRNAs) induce sequence-specific silencing in mammalian cells," Genes Dev., vol. 16, pp. 948-958 (2002).
Page, K. A., et al., "Construction and Use of a Human Immunodeficiency Virus Vector for Analysis of Virus Infectivity," J. Virol., vol. 64, No. 11, pp. 5270-5276 (Nov. 1990).
Parmacek, Michael S., "MicroRNA-modulated targeting of vascular smooth muscle cells," The Journal of Clinical Investigation, vol. 119, No. 9, pp. 2526-2528 (Sep. 2009).
Paul, C. P., et al., "Effective expression of small interfering RNA in human cells" Nat. Biotechnol., vol. 20, No. 5, pp. 505-508, 6 pages (May 2002).
Peppas, N. A., et al., "Hydrogels in Biology and Medicine: From Molecular Principles to Bionanotechnology," Adv. Mater., vol. 18, pp. 1345-1360 (2006).
Petropoulos, C. J., et al., "Using Avian Retroviral Vectors for Gene Transfer," J. Virol., vol. 66, No. 6, pp. 3391-3397 (Jun. 1992).
Poon, M., et al., "Rapamycin Inhibits Vascular Smooth Muscle Cell Migration," J. Clin Invest, vol. 98, No. 10, pp. 2277-2283 (Nov. 1996).
Porter, D. L., et al., "Chimeric Antigen Receptor—Modified T Cells in Chronic Lymphoid Leukemia," NEJM, vol. 365, No. 8, pp. 725-733, 12 pages (Aug. 25, 2011).
Quantin, B., et al., "Adenovirus as an expression vector in muscle cells in vivo," Proc. Natl. Acad. Sci. USA, vol. 89, No. 7, pp. 2581-2584 (Apr. 1992).
Quintavalle, M., et al., "MicroRNA control of podosome formation in vascular smooth muscle cells in vivo and in vitro," The Journal of Cell Biology, vol. 189, No. 1, pp. 13-22 (Mar. 29, 2010).
Rabinowitz, J. E., et al., "Cross-Packaging of a Single Adena-Associated Virus (AAV) Type 2 Vector Genome into Multiple AAV Serotypes Enables Transduction with Broad Specificity," J. Virol., vol. 76, No. 2, pp. 791-801 (Jan. 2002).
Roberts, O. L., et al., "ERK5 and the regulation of endothelial cell function," Biochemical Society Transactions, vol. 37, part 6, pp. 1254-1259 (2009).
Rosenfeld, M. A., et al., "In Vivo Transfer of the Human Cystic Fibrosis Transmembrane Conductance Regulator Gene to the Airway Epithelium," Cell, vol. 68, No. 1, pp. 143-155 (Jan. 10, 1992).
Samulski, R. J., et al., "A Recombinant Plasmid from Which an Infectious Adena-Associated Virus Genome Can be Excised In Vitro and Its Use to Study Viral Replication," J. Virol., vol. 61, No. 10, pp. 3096-3101 (Oct. 1987).
Samulski, R. J., et al., "Helper-Free Stocks of Recombinant Adena-Associated Viruses: Normal Integration Does Not Require Viral Gene Expression," J. Virol., vol. 63, No. 9, pp. 3822-3828 (Sep. 1989).
Santulli, G., et al., "CaMK4 Gene Deletion Induces Hypertension," J. Am. Heart Assoc., vol. 1, e001081, pp. 1-15 (2012).
Santulli, G., et al., "Evaluation of the anti-angiogenic properties of the new selective alphaVbeta3 integrin antagonist RGDechHCit," J. Transl. Med., vol. 9, pp. 1-10 (2011).
Santulli, G., et al., "In vivo properties of the proangiogenic peptide QK," J. Transl. Med., vol. 7, pp. 1-10 (2009).
Shimada, T., et al., "Targeted and Highly Efficient Gene Transfer into CD4 Cells by a Recombinant Human Immunodeficiency Virus Retroviral Vector," J. Clin. Invest., vol. 88, No. 3, pp. 1043-104 7 (1991).
Shivdasani, R. A., "MicroRNAs: regulators of gene expression and cell differentiation," Blood, vol. 108, No. 12, pp. 3646-3653 (Dec. 1, 2006).
Sorge, J., et al., "Amphotropic Retrovirus Vector System for Human Cell Gene Transfer," Mol. Cell Biol., vol. 4, No. 9, pp. 1730-1737 (Sep. 1984).
Sousa, J. E., et al., "Lack of Neointimal Proliferation After Implantation of Sirolimus-Coated Stents in Human Coronary Arteries: A Quantitative Coronary Angiography and Three-Dimensional Intravascular Ultrasound Study," Circulation, vol. 103, pp. 192-195, 4 pages (2001).
Stettler, C., et al., "Outcomes associated with drug-eluting and bare-metal stents: a collaborative network meta-analysis," Lancet, vol. 370, pp. 937-948, 12 pages (Sep. 15, 2007).
Stone, G. W., et al., "A Polymer-Based, Paclitaxel-Eluting Stent in Patients with Coronary Artery Disease," The New England Journal of Medicine, vol. 350, No. 3, pp. 221-231 (Jan. 15, 2004).
Strafford-Perricaudet, L. D., et al., "Evaluation of the transfer and expression in mice of an enzyme-encoding gene using a human adenovirus vector," Hum. Gene Ther., vol. 1, No. 3, pp. 241-256, 24 pages (Fall 1990).
Totary-Jain, H., et al., "Rapamycin resistance is linked to defective regulation of Skp2," Cancer Res., vol. 72, No. 7, pp. 1836-1843, 14 pages (Apr. 1, 2012).
Tuschl, Thomas, "Expanding small RNA interference," Nat. Biotechnol., vol. 20, pp. 446-448 (May 2002).
Urbich, C., et al., "Role of microRNAs in vascular diseases, inflammation, and angiogenesis," Cardiovascular Research, vol. 79, pp. 581-588 (2008).
Van Den Heuvel, M., et al., "Endothelial dysfunction after drug eluting stent implantation," Minerva Cardioangiol., vol. 57, No. 5, pp. 629-643 (2009).
Van Rooij, E. and Olson, E. N., "MicroRNA therapeutics for cardiovascular disease: opportunities and obstacles," Nat. Rev. Drug Discovery, vol. 11, pp. 860-872 (Nov. 2012).
Van Rooij, E., et al., "Toward MicroRNA-Based Therapeutics for Heart Disease: The Sense in Antisense," Circulation Research, vol. 103, pp. 919-928 (2008).
Verma, Inder M., "Gene Therapy," Scientific American, pp. 68-72, 81-82 and 84 (Nov. 1990).
Vestweber, Dietmar, "VE-cadherin: the major endothelial adhesion molecule controlling cellular junctions and blood vessel formation," Arterioscler Thromb. Vase. Biol., vol. 28, pp. 223-232 (2008).
Vickers, K. C. and Remaley, A. T., "MicroRNAs in atherosclerosis and lipoprotein metabolism," Current Opinion in Endocrinology, Diabetes, and Obesity, vol. 17, pp. 150-155, 6 pages (2010).
Violaris, A.G., et al., "Influence of serum cholesterol and cholesterol subtractions on restenosis following successful coronary intervention," Semin. Interv. Cardiol., vol. 4, No. 3, pp. 111-119 (Sep. 1999).
Waehler, R., et al., "Engineering targeted viral vectors for gene therapy," Nat. Rev. Genet., vol. 8, No. 8, pp. 573-587 (Aug. 2007).
Wang S. et al., "The Endothelial-Specific MicroRNA miR-126 Governs Vascular Integrity and Angiogenesis" Dev. Cell, vol. 15, No. 2, pp. 261-271 (Aug. 12, 2008).

(56) References Cited

OTHER PUBLICATIONS

Wang, X., et al., "Repression of Versican Expression by MicroRNA-143," Journal of Biological Chemistry, vol. 285, No. 30, pp. 23241-23250 (Jul. 23, 2010).

Welt, F. G. P. & Rogers, C., "Inflammation and Restenosis in the Stent Era," Arterioscler. Thromb. Vase. Biol., vol. 22, pp. 1769-1776 (2002).

Wenaweser, P., et al., "Incidence and Correlates of Drug-Eluting Stent Thrombosis in Routine Clinical Practice," Journal of the American College of Cardiology, vol. 52, No. 14, pp. 1134-1140 (2008).

Wijns, William, "Late stent thrombosis after drug-eluting stent: seeing is understanding" Circulation, vol. 120, No. 5, pp. 364-365 (2009).

Wilkinson, G. W. G. and Akrigg, A., "Constitutive and enhanced expression from the CMV major IE promoter in a defective adenovirus vector," Nucleic Acids Res., vol. 20, No. 9, pp. 2233-2239 (1992).

Xia, H., et al., "siRNA-mediated gene silencing in vitro and in vivo," Nat. Biotechnol., vol. 20, pp. 1006-1010 (Oct. 2002).

Yamaguchi, K., et al., "Local persistent hypercoagulability after sirolimus-eluting stent implantation in patients with stable angina," Int. J. Cardiol., vol. 153, pp. 272-276 (Dec. 15, 2011).

Zeng, Y., et al., "Both Natural and Designed Micro RNAs Can Inhibit the Expression of Cognate mRNAs When Expressed in Human Cells," Molecular Cell, vol. 9, pp. 1327-1333 (Jun. 2002).

Zhang, B., et al., "microRNAs as oncogenes and tumor suppressors," Dev. Biol., vol. 302, No. 1, pp. 1-12 (2007).

Zhang, Chunxiang, "MicroRNA and vascular smooth muscle cell phenotype: new therapy for atherosclerosis?" Genome Medicine, vol. 1, pp. 85-85.3 (2009).

Zhu et al. (Journal of Biological Chemistry. May 11, 2007; 282(19: 14328-14336).

Santulli et al., A selective microRNA-based strategy inhibits restenosis while preserving endothelial function, JCI, vol. 124, No. 9, p. 4102-4114, 2014.

* cited by examiner

SMOOTH MUSCLE SPECIFIC INHIBITION FOR ANTI-RESTENOTIC THERAPY

CROSS-REFERENCE TO RELATED APPLICATIONS

This application is a divisional application of U.S. patent application Ser. No. 14/390,988, filed on Oct. 6, 2014, which is a U.S. National Phase application under 35 U.S.C. § 371 of International Patent Application No. PCT/US2013/035327, filed on Apr. 4, 2013, which claims the benefit of and priority under 35 U.S.C. § 119(e) to U.S. Provisional Application No. 61/620,404, filed on Apr. 4, 2012, and U.S. Provisional Application No. 61/727,003, filed on Nov. 15, 2012. The contents of these applications are incorporated by reference herein in their entireties and for all purposes.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosure of these publications in their entireties are hereby incorporated by reference into this application in order to more fully describe the state of the art as know to those skilled therein as of the dat of the invention described herein.

GOVERNMENT SUPPORT

This invention was made with government support under Grant No. K99HL109133-01 awarded by the National Institute of Health. The Government has certain rights in the invention.

SEQUENCE LISTING

This instant application contains a Sequence Listing which has been submitted in ASCII format via EFS-Web and is hereby incorporated by reference in its entirety. Said ASCII copy, created in Mar. 20, 2015, is named "13B196PR2-210112-9059-US04-SEQ-LIST-11-07-17.txt", and is 7,466 bytes in size.

BACKGROUND

The high incidence of cardiovascular diseases represents a significant medical problem in the USA and throughout the world, despite remarkable advances over the past few decades. From the 1990's to early 2000's, restenosis after balloon angioplasty and/or stent implantation occurred with an incidence of approximately 50% and 25%, respectively, leading to a significant limitation in its effectiveness.

A major advance in the treatment of coronary artery disease (CAD) emerged from studies showing that rapamycin was a potent inhibitor of proliferation and migration of VSMCs, and led to the development of rapamycin-coated stents (Cypher) which markedly reduced restenosis and revolutionized the field of percutaneous coronary intervention (PCI).

Percutaneous coronary intervention (PCI) is one of the most commonly performed interventions that have transformed the practice of revascularization for CAD. However, the major drawback of this procedure is the proliferation and subsequent accumulation of vascular smooth muscle cells (VSMC), leading to restenosis. The advent of drug eluting stents, capable of delivering an inhibitor of cell proliferation in situ has decreased, but not eliminated, the occurrence of restenosis. The drugs that elute from the stent not only inhibit VSMC, but also EC proliferation and migration, increasing the risk of late thrombosis. Thus, there is a need for therapies that would provide VSMC selective antiproliferative activity without affecting EC.

SUMMARY OF THE INVENTION

The present invention provides for the incorporation of target sequences for a microRNA into the 3'-UTR of a gene, such as, but not limited to, a tumor suppressor gene, that is present in an expression vector. The expression vector is used to specifically over-express the gene in one cell type that either does not express the microRNA, or has very low expression levels of the microRNA, while inhibiting the expression of the gene in another cell type that has higher expression levels of the microRNA.

In one aspect, the present invention provides a nucleic acid vector comprising a gene of interest and one or more target sequences for a microRNA within the 3' UTR region of the gene of interest. In one embodiment, the gene of interest is the p27 gene. In one embodiment, the microRNA is miR-126. In one embodiment, the one or more target sequences comprise SEQ ID NO:2. In one embodiment, the vector comprises four target sequences for a microRNA. In another embodiment, the target sequences for a microRNA are identical. In one embodiment, the target sequences for a microRNA comprise SEQ ID NO:2.

In another embodiment, the vector comprises a second gene of interest. In another embodiment, the vector comprises one or more target sequences for a microRNA within the 3' UTR region of the second gene of interest.

In another embodiment, the nucleic acid vector is a viral vector. In yet another embodiment, the viral vector is an adenoviral vector. In another embodiment, the vector is delivered to a cell of interest. In one embodiment, the cell of interest is an endothelial cell.

In another aspect, the invention provides an expression system comprising a nucleic acid vector, wherein the nucleic acid vector comprises a gene of interest, and one or more target sequences for a microRNA within the 3' UTR region of the gene of interest. In one embodiment, the gene of interest is the p27 gene. In one embodiment, the microRNA is miR-126. In one embodiment, the one or more target sequences comprise SEQ ID NO:2. In one embodiment, the vector comprises four target sequences for a microRNA. In another embodiment, the target sequences for a microRNA are identical. In one embodiment, the target sequences for a microRNA comprise SEQ ID NO:2.

In another embodiment, the vector comprises a second gene of interest. In another embodiment, the vector comprises one or more target sequences for a microRNA within the 3' UTR region of the second gene of interest. In another embodiment, the nucleic acid vector is a viral vector. In yet another embodiment, the viral vector is an adenoviral vector.

In another aspect, the invention provides a cell comprising a nucleic acid vector, wherein the nucleic acid vector comprises a gene of interest, and one or more target sequences for a microRNA within the 3' UTR region of the gene of interest. In one embodiment, the gene of interest is the p27 gene. In one embodiment, the microRNA is miR-126. In one embodiment, the one or more target sequences comprise SEQ ID NO:2. In one embodiment, the vector comprises four target sequences for a microRNA. In another embodiment, the target sequences for a microRNA are identical. In one embodiment, the target sequences for a microRNA comprise SEQ ID NO:2.

In one embodiment, the vector comprises a second gene of interest. In another embodiment, the vector comprises one or more target sequences for a microRNA within the 3' UTR region of the second gene of interest. In one embodiment, the nucleic acid vector is a viral vector. In yet another embodiment, the viral vector is an adenoviral vector. In one embodiment, the cell is an endothelial cell. In another embodiment, the cell is a vascular smooth muscle cell.

In one aspect, the invention provides a pharmaceutical composition comprising a nucleic acid vector, wherein the nucleic acid vector comprises a gene of interest, and one or more target sequences for a microRNA within the 3' UTR region of the gene of interest. In one embodiment, the gene of interest is the p27 gene. In one embodiment, the microRNA is miR-126. In one embodiment, the one or more target sequences comprise SEQ ID NO:2. In one embodiment, the vector comprises four target sequences for a microRNA. In another embodiment, the target sequences for a microRNA are identical. In one embodiment, the target sequences for a microRNA comprise SEQ ID NO:2.

In one embodiment, the vector comprises a second gene of interest. In another embodiment, the vector comprises one or more target sequences for a microRNA within the 3' UTR region of the second gene of interest. In another embodiment, the nucleic acid vector is a viral vector. In yet another embodiment, the viral vector is an adenoviral vector.

In another aspect, the invention provides a method of treating or preventing a cardiovascular disease in a subject in need thereof, the method comprising administering a nucleic acid vector to the subject, wherein the nucleic acid vector comprises a gene of interest and one or more target sequences for a microRNA within the 3' UTR region of the gene of interest. In one embodiment, the gene of interest is the p27 gene. In one embodiment, the microRNA is miR-126. In one embodiment, the one or more target sequences comprise SEQ ID NO:2. In one embodiment, the vector comprises four target sequences for a microRNA. In another embodiment, the target sequences for a microRNA are identical. In one embodiment, the target sequences for a microRNA comprise SEQ ID NO:2.

In one embodiment, the vector comprises a second gene of interest. In another embodiment, the vector comprises one or more target sequences for a microRNA within the 3' UTR region of the second gene of interest. In another embodiment, the nucleic acid vector is a viral vector. In yet another embodiment, the viral vector is an adenoviral vector.

In one embodiment, the nucleic acid vector is delivered into a cell of the subject. In another embodiment, the cell expresses the microRNA. In one embodiment, the gene of interest is not expressed in the cell. In one embodiment, the cell is an endothelial cell. In another embodiment, the cell is a vascular smooth muscle cell. In one embodiment, the cardiovascular disease is coronary artery disease.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The patent or application file contains at least one drawing executed in color. Copies of this patent or patent application publication with color drawing(s) will be provided by the United States Patent and Trademark Office upon request and payment of the necessary fee.

BRIEF DESCRIPTION OF THE FIGURES

FIG. 1A. Control CMV virus (CMV) FIG. 1B. p27 expressing adenovirus under the control of CMV promoter (p27). FIG. 1C. p27 expressing adenovirus under the control of CMV promoter, containing four target sequences for mir-126 in their 3'UTR (p27-126TS). FIG. 1D. Representative immunoblots for the indicated proteins from VSMC or HUVEC infected with adenovirus described in A-C at 20 pfu/cell or 50 pfu/cell respectively for 48 hr.

FIG. 2A. Real Time qRT-PCR analysis of miR-126 (FIGS. 2B-C) Representative immunoblot of three independent experiments quantified by densitometry. FIG. 2D. Proliferation assays of VSMC and EC infected with the indicated Ad. Migration assays of VSMC (FIGS. 2E, F) and EC (FIGS. 2G, H) infected with the indicated Ad; representative pictures at the indicated time points are shown.

FIGS. 2I, J. Network formation assay in EC. Orange scale bar indicates 100 µm (magnification 4×). All data shown are means±s.e.m. from at least three experiments performed in quadruplets. Data comparisons were made using one way analysis of variance with Bonferroni post hoc tests; *P<0.01 versus VSMC (FIG. 2A);*P<0.01 versus Ad-GFP (FIGS. 2C, D, F, H, J).

FIG. 3A. Representative sections of rat carotid arteries immunostained for smooth muscle cell actin (aSMA) and for the specific EC marker VE-Cadherin (VE-Cad). Nuclei were counterstained with DAPI. No positive staining was observed in the negative control sections. Orange scale bars: 100 µm (magnification 60×, inlays show high magnification images), arrowheads indicate EC beyond the inner autofluorescent elastic laminae. FIG. 3B. Neointima/media ratios and (FIG. 3C) endothelial coverage were calculated from 5 rats/group. FIG. 3D. Plasma levels of D-dimer in plasma collected before (uninjured) and 2 weeks after the balloon injury using a specific rat immunoassay; n=4 rats/group. FIG. 3E. Vascular reactivity analysis on carotid rings showing the vasodilatative response to acetylcholine (ACh); n=3 rats/group. All the data are means±s.e.m. from at least three experiments performed in triplicate. Data comparison was made using one way (FIGS. 3B-D) or two-way repeated measures (FIG. 3E) analysis of variance with Bonferroni post hoc tests; *P<0.01 versus uninjured.

FIG. 4A. The Ad-GFP contains only the sequence for GFP. FIG. 4B. The Ad-p27 contains the sequences for GFP and p27. FIG. 4C. The Ad-p27-126TS contains GFP and p27 that have four target sequences for miR-126 in its 3'UTR.

FIG. 5A. To overcome the autofluorescence issues typical of the vascular sections, the efficiency of the Ad infection was evaluated by using a primary antibody against GFP, revealed by a Cy3-conjugated secondary antibody. Representative digital images are shown. Orange scale bar represents 100 μm (magnification 60×). FIG. 5B. Representative sections stained with hematoxilyn/eosin (magnification 10×, inlays show the whole arterial section in a 5× magnification; orange scale bar represents 500 μm).

DETAILED DESCRIPTION OF THE INVENTION

Figures 1A, 1B, 1C, 1D:
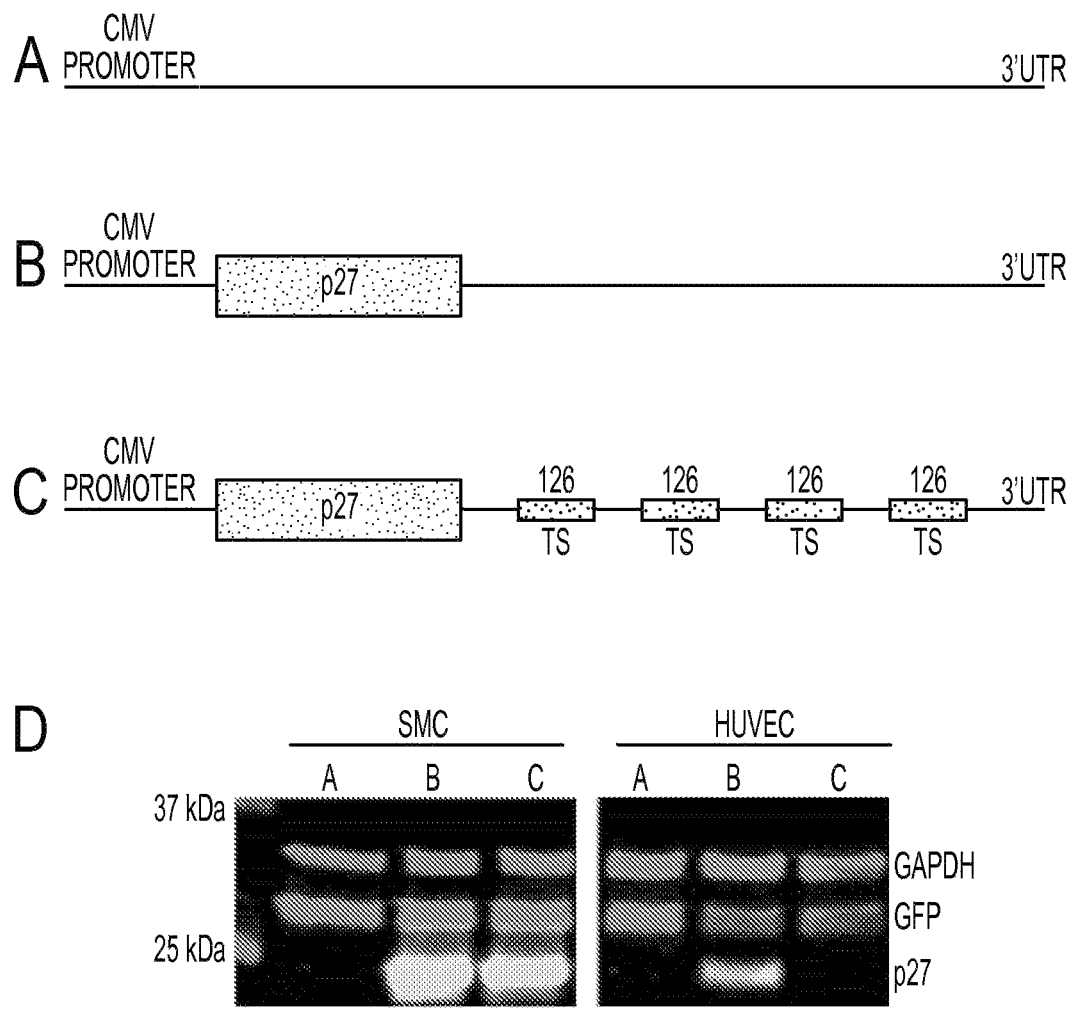
FIGS. 1A-D. Schematic representation of p27-expressing viruses.

The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference.

As would be apparent to one of ordinary skill in the art, any method or composition described herein can be implemented with respect to any other method or composition described herein.

Abbreviations and Definitions

As used herein, the term "p27" refers to the cyclin-dependent kinase inhibitor also known as p27Kip1, which is a member of the kinase inhibitor protein (KIP) family. p27 is a protein encoded by the CDKN1B gene. The nucleic acid sequences of the gene encoding p27, including, but not limited to, the nucleic acid sequence of the open reading frame of the gene, is known in the art. The nucleic acid sequences of the gene encoding human p27, including, but not limited to, the nucleic acid sequence of the open reading frame of the human gene, is known in the art. The amino acid sequences of the p27 polypeptide and protein, including, but not limited to, the amino acid sequences of the human p27 polypeptide and proteins, are known in the art. The GeneBank accession number of the nucleic acid sequence of human p27 is NM_004064. The GeneBank accession number of the amino acid sequence of human p27 is NP_004055. For additional information on p27, see e.g., Nisar P. Malek, Holly Sundberg, Seth McGrew, Keiko Nakayama, Themis R. Kyriakidis & James M. Roberts, 2001, A mouse knock-in model exposes sequential proteolytic pathways that regulate p27Kip1 in G1 and S phase, Nature, 413, 323-327. p27 is also known as KIP!; MEN4; CDKN4, MEN1B and P27KIP1.

As used herein, the term "miR-126" refers to microRNA 126. The nucleic acid sequence of miR-126 is known in the art. The nucleic acid sequences of human miR-126 is known in the art. The GeneBank accession number of the nucleic acid sequence of human miR-126 is M1 0000471.

As used herein, the abbreviation "HUVEC" refers to Human Umbilical Venous Endothelial Cells.

As used herein, the abbreviation "EC" refers to Endothelial Cells.

As used herein, the abbreviation "VSMC" refers to Vascular Smooth Muscle Cells.

As used herein, the abbreviation "SMC" refers to smooth muscle cells.

The singular forms "a," "an," and "the" include plural reference unless the context clearly dictates otherwise.

The use of the word "a" or "an" when used in conjunction with the term "comprising" in the claims and/or the specification may mean "one," but it is also consistent with the meaning of "one or more," "at least one." and "one or more than one."

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

DETAILED DESCRIPTION

Treatment of Coronary Artery Disease

Cardiovascular disease accounts for nearly one third of deaths globally, and Coronary Artery Disease (CAD) remains the number one cause of death in the United States (Heron M, Hoyert D L, Murphy S L, Xu J, Kochanek K D, Tejada-Vera B: Deaths: final data for 2006. Natl Vital Stat Rep 57(14), 1-134 (2009)).

The introduction of the Drug-Eluting Stent (DES) has revolutionized the field of angioplasty, by significantly reducing rates of restenosis when compared to bare-metal stents (BES) (Marks A R: Sirolimus for the prevention of in-stentrestenosis in a coronary artery. N Engl J Med 349 (14), 1307-1309 (2003). The anti-restenotic action of the drug (Sirolimus or rapamycin) lies at least in part, on its ability to up-regulate levels of p27, a widely expressed protein that inhibits cyclin-dependent kinases (cdks) complexes in G1 and S phases (Marx S O, Totary-Jain H, Marks A R: Vascular smooth muscle cell proliferation in restenosis. Circ Cardiovasc Interv 4(1), 104-111 (2011). Despite the significant improvement, drug-eluting stents (DES) hike the risk of late stent thrombosis by about 0.2% over bare-metal stents and is associated with long-term myocardial infarction and death rates (Garg S, Serruys P W: Coronary stents: looking forward. J Am Coll Cardiol 56(10 Suppl). S43-78 (2010): Wijns W: Late stent thrombosis after drug-eluting stent: seeing is understanding. Circulation 120(5), 364-365 (2009)). Delayed endothelial coverage after DES implantation is thought to prolong the window of vulnerability to stent thrombosis, which requires a prolonged dual anti-platelet therapy (Van Den Heuvel M, Sorop 0, Van Beusekom H M, Van Der Giessen W J: Endothelial dysfunction after drug eluting stent implantation. Minerva Cardioangiol 57(5), 629-643 (2009)).

The current generation of DES that elute non selective drugs from their surfaces to reduce smooth muscle cell growth also inhibit endothelialisation (Finn A V, Nakazawa G, Joner M et al.: Vascular responses to drug eluting stents: importance of delayed healing. Arterioscler Thromb Vasc Biol 27(7), 1500-1510 (2007); Joner M, Finn A V, Farb A et al.: Pathology of drug-eluting stents in humans: delayed healing and late thrombotic risk. J Am Coll Cardiol 48(1), 193-202 (2006)).

Newer stents and coronary devices are currently undergoing pre-clinical and clinical trials including DES with biodegradable polymers, polymer free DES, new coated stents, completely biodegradable stents, bifurcation stents and drug-eluting balloons. However, these new approaches continue to utilize non-selective antiproliferative drugs that inhibit both vascular smooth muscle cells (VSMC) and vascular endothelial cell (EC) proliferation, adversely affecting critical endothelial cell functions such as maintaining vascular tone, providing a permeable barrier, modulating adhesion, inflammation and thrombosis. Therefore, it is of paramount importance to develop therapeutic strategies that can selectively inhibit VSMC and other infiltrated cells without affecting EC functions. The present invention addresses this need.

The present invention provides for the incorporation of target sequences for a microRNA into the 3'-UTR of a gene, such as, but not limited to, a tumor suppressor gene, that is present in an expression vector. The expression vector is used to specifically over-express the gene in one cell type that either does not express the microRNA, or has very low expression levels of the microRNA, while inhibiting the expression of the gene in another cell type that has higher expression levels of the microRNA.

In one embodiment, the present invention provides for the incorporation of target sequences for the VEC-specific miRNA, miR-126, into the 3'-UTR of p27 in a p27-expressing vector, to specifically over-express p27 in vascular smooth muscle cells (VSMC), without affecting endothelial cells (EC) that express mir-126 at higher levels than VSMC. This strategy will result in the specific inhibition of VSMC proliferation, migration and neointimal formation, without affecting endothelial cells, because p27-expressing vectors will be targeted for degradation in endothelial cells.

The invention can be used, for example, in conjunction with BMS implantation to provide the benefits of a DES without the concern of DES post-operative complications. The invention can be used, for example, for the inhibition of VSMC proliferation in altherosclerosis and arterial injury, as well as vascular access failure in hemodialysis patients.

MicroRNAs

A variety of nucleic acid species are capable of modifying gene expression. These include antisense RNA, siRNA, microRNA, RNA and DNA aptamers, and decoy RNAs. Each of these nucleic acid species can inhibit target nucleic acid activity, including gene expression.

MicroRNAs (miRNAs or miRs) are a class of short (18-25 nt) non-coding RNAs (ncRNAs) that exist in a variety of organisms, including mammals, and are conserved in evolution. miRNAs are processed from hairpin precursors of 70 nt (pre-miRNA) which are derived from primary transcripts (pri-miRNA) through sequential cleavage by the RNAse III enzymes drosha and dicer. miRNAs can be encoded in intergenic regions, hosted within introns of pre-mRNAs or within ncRNA genes. Many miRNAs also tend to be clustered and transcribed as polycistrons and often have similar spatial temporal expression patterns. miRNAs have been found to have roles in a variety of biological processes including developmental timing, differentiation, apoptosis, cell proliferation, organ development, and metabolism.

At least 222 separate miRNA genes have been identified in the human genome. For example, 2 miRNA genes (miR15a and miR16a) have been localized to a homozygously deleted region on chromosome 13 that is correlated with chronic lymphocytic leukemia (Calin et al. (2002), Proc. Natl. Acad. Sci. USA 99:15524-29). However, the distribution of miRNA genes throughout the genome, and the relationship of the miRNA genes to diverse chromosomal features, has not been systematically studied. A further review of miRNAs is provided in U.S. Pat. No. 7,232,806, U.S. Patent Application Publication No. 2006/0105360, and in the references: Landgraf et al., 2007, *Cell* 129: 1401-1414; Mendell, J T, 2005 *Cell Cycle* 4(9):1179-84; Shivdasani R A, 2006 Blood 108(12):3646-53; Hwang and Mendell, 2006 *Br J Cancer* 94(6):776-80; Hammond S M, 2006: *Curr Opin Genet Dev.* 16(1):4-9; Osada and Takahashi, 2007 *Carcinogenesis* 28(1): 2-12; and Zhang et al., 2007 *Dev Biol.* 302(1):1-12, all of which are hereby incorporated by reference in their entirety.

MicroRNAs can inhibit target nucleic acid activity, including gene expression. For example, miRNAs can function via base paring with complementary nucleic acid sequences within mRNA molecules. The pairing of miRNAs with complementary mRNA molecules usually results in gene silencing via translational repression or target degradation. Animal miRNAs can exhibit only partial complementarity to their mRNA targets. A seed region of about 6-8 nucleotides in length at the 5' end of an miRNA is thought to be an important determinant of target specificity. A given miRNA can have multiple different mRNA targets and a given target can be targeted by multiple miRNAs. For additional information on miRNAs, see also Ishida el al., 2013, miRNA-Based Therapeutic Strategies, *Curr Anesthesiol Rep.*, 1(1):63-70, which is incorporated herein by reference in its entirety.

Nucleic Acid Vectors and Expression Systems

In one aspect, the present invention provides a nucleic acid vector comprising a gene of interest, and one or more target sequences for a microRNA within the 3' UTR region of the gene of interest.

In one embodiment, the gene of interest is a human gene. In another embodiment, the gene of interest is a nonhuman gene. In one embodiment, the gene of interest is a p27 gene. In another embodiment, the gene of interest is p53. In other embodiments, the gene of interest is a tumor suppressor gene. A tumor suppressor gene can include, but is not limited to, APC, RBI, INK4, PTEN, MADR2, BRAC1, BRAC2, or DPC4.

In one embodiment, the microRNA is miR-126. In another embodiment, the microRNA is miR-143. In another embodiment, the micro-RNA is miR-145. In further embodiments, the microRNA is Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the one or more target sequences comprise SEQ ID NO:2. In another embodiment, the one or more target sequences do not comprise SEQ ID NO:2. In another embodiment, the one or more target sequences comprise a nucleic acid sequence complementary to SEQ ID NO:2. In another embodiment, the one or more target sequences do not comprise a nucleic acid sequence complementary to SEQ ID NO:2.

In one embodiment, the vector comprises four target sequences for a microRNA. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the target sequences for a microRNA are identical. In another embodiment, the target sequences for a microRNA are not identical. The nucleic acid vectors can comprise different combinations of target sequences for various microRNAs, including, but not limited to, miR-126, miR-143, miR-145, Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the target sequences for a microRNA comprise SEQ ID NO:2. In another embodiment, the target sequences for a microRNA do not comprise SEQ ID NO:2. In another embodiment, the target sequences for a microRNA comprise a nucleic acid sequence complementary to SEQ ID NO:2. In another embodiment, the target sequences for a microRNA do not comprise a nucleic acid sequence complementary to SEQ ID NO:2.

In another embodiment, the vector comprises a second gene of interest. In one embodiment, the second gene of interest is a human gene. In another embodiment, the second gene of interest is a non-human gene. In one embodiment, the second gene of interest is p53. In other embodiments, the second gene of interest is a tumor suppressor gene. A tumor suppressor gene can include, but is not limited to, APC, RB 1, INK4, PTEN, MADR2, BRAC1, BRAC2, or DPC4. In one embodiment, the second gene of interest is an anti-thrombotic gene. In another embodiment, the second gene of interest is an anti-inflammatory gene. In another embodiment, the second gene of interest is ENTPD1, TFPI or PTGIS.

In another embodiment, the vector comprises one or more target sequences for a microRNA within the 3' UTR region of the second gene of interest. In one embodiment, the vector comprises one target sequence. In another embodiment, the vector comprises two target sequences. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the nucleic acid vector is a viral vector. In one embodiment, the viral vector is an adenoviral vector. In another embodiment, the viral vector is a lentiviral vector. In one embodiment, the vector is a retroviral vector. In another embodiment, is an oncoviral vector. Examples of adenoviral vectors include vectors derived from adenoviruses such as, but not limited to, adenovirus type 2 (Ad2), adenovirus type 5 (Ad5), adenovirus type 7 (Ad7) and adenovirus type 12 (Ad12). In a further embodiment, the vector is an adeno-associated vector. Examples of adeno-associated vector includes vectors derived from adeno-associated viruses such as, but not limited to, adeno-associated virus type 1 (AAV1), adeno-associated virus type 2 (AAV2), adeno-associated virus type 4 (AAV4), adeno-associated virus type 5 (AAV5), adeno-associated virus type 6 (AAV6), adeno-associated virus type 7 (AAV7), and adeno-associated virus type 2 (AAV2). Examples of lentiviral vectors include vectors derived from lentiviruses such as, but not limited to, HIV-1 and HIV-2. Examples of retroviral vectors include vectors derived from retroviruses such as, but not limited to, Moloney murine leukemia virus (MMLV). Examples of oncoviral vectors include vectors derived from oncoviruses such as, but not limited to, Murine Leukemia Virus (MLV), Spleen Necrosis Virus (SNV), Rous sarcoma virus (RSV) and Avian Leukosis Virus (ALV).

In another embodiment, the vector is delivered to a cell of interest. Delivery can be conducted by any method known to one of skill in the art, including, but not limited to, injection, transfection, lipofection, microinjection, calcium phosphate or calcium chloride precipitation, DEAE-dextrin-mediated transfection, or electroporation. Electroporation is carried out at approximate voltage and capacitance to result in entry of the DNA construct(s) into cells of interest. Other methods used to transfect cells can also include modified calcium phosphate precipitation, polybrene precipitation, liposome fusion, and receptor-mediated gene delivery.

In one embodiment, the cell of interest is an endothelial cell. In another embodiment, the cell of interest is a vascular smooth muscle cell. In further embodiments, the cell may be from the germ line or somatic, totipotent or pluripotent, dividing or non-dividing, parenchyma or epithelium, immortalized or transformed, or the like. The cell may be a stem cell or a differentiated cell. Cell types that are differentiated include, but are not limited to, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine and exocrine glands.

In another embodiment, the cell of interest is a cancer cell. The cancer can be, but is not limited to, breast cancer, lung cancer, kidney cancer, brain cancer, liver cancer, colorectal cancers, progressive lung adenocarcinoma, lymphomas, leukemias, adenocarcinomas and sarcomas.

In another aspect, the invention provides an expression system comprising a nucleic acid vector, wherein the nucleic acid vector comprises a gene of interest and one or more target sequences for a microRNA within the 3' UTR region of the gene of interest.

In one embodiment, the gene of interest is a human gene. In another embodiment, the gene of interest is a nonhuman gene. In one embodiment, the gene of interest is a p27 gene. In another embodiment, the gene of interest is p53. In other embodiments, the gene of interest is a tumor suppressor gene. A tumor suppressor gene can include, but is not limited to, APC, RBI, INK4, PTEN, MADR2, BRAC1, BRAC2, or DPC4.

In one embodiment, the microRNA is miR-126. In another embodiment, the micro-RNA is miR-143. In another embodiment, the micro-RNA is miR-145. In further embodiments, the microRNA is Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the one or more target sequences comprise SEQ ID NO:2. In another embodiment, the one or more target sequences do not comprise SEQ ID NO:2. In another embodiment, the one or more target sequences comprise a nucleic acid sequence complementary to SEQ ID NO:2. In another embodiment, the one or more target sequences do not comprise a nucleic acid sequence complementary to SEQ ID NO:2.

In one embodiment, the vector comprises four target sequences for a microRNA. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the target sequences for a microRNA are identical. In another embodiment, the target sequences for a microRNA are not identical. The nucleic acid vectors can comprise different combinations of target sequences for various microRNAs, including, but not limited to, miR-126, miR-143, miR-145, Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the target sequences for a microRNA comprise SEQ ID NO:2. In another embodiment, the target sequences for a microRNA do not comprise SEQ ID NO:2. In another embodiment, the target sequences for a microRNA comprise a nucleic acid sequence complementary to SEQ ID NO:2. In another embodiment, the target sequences for a microRNA do not comprise a nucleic acid sequence complementary to SEQ ID NO:2.

In another embodiment, the vector comprises a second gene of interest. In one embodiment, the second gene of interest is a human gene. In another embodiment, the second gene of interest is a non-human gene. In one embodiment, the second gene of interest is p53. In other embodiments, the second gene of interest is a tumor suppressor gene. A tumor suppressor gene can include, but is not limited to, APC, RB 1, INK4, PTEN, MADR2, BRAC1, BRAC2, or DPC4. In one embodiment, the second gene of interest is an antithrombotic gene. In another embodiment, the second gene of interest is an anti-inflammatory gene. In another embodiment, the second gene of interest is ENTPD1, TFPI or PTGIS.

In another embodiment, the vector comprises one or more target sequences for a microRNA within the 3' UTR region of the second gene of interest. In one embodiment, the vector comprises one target sequence. In another embodiment, the vector comprises two target sequences. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the nucleic acid vector is a viral vector. In one embodiment, the viral vector is an adenoviral vector. In another embodiment, the viral vector is a lentiviral vector. In one embodiment, the vector is a retroviral vector. In another embodiment, is an oncoviral vector. Examples of adenoviral vectors include vectors derived from adenoviruses such as, but not limited to, adenovirus type 2 (Ad2), adenovirus type 5 (Ad5), adenovirus type 7 (Ad7) and adenovirus type 12 (Ad12). In a further embodiment, the vector is an adeno-associated vector. Examples of adeno-associated vector includes vectors derived from adeno-associated viruses such as, but not limited to, adeno-associated virus type 1 (AAV1), adeno-associated virus type 2 (AAV2), adeno-associated virus type 4 (AAV4), adeno-associated virus type 5 (AAV5), adeno-associated virus type 6 (AAV6), adeno-associated virus type 7 (AAV7), and adeno-associated virus type 2 (AAV2). Examples of lentiviral vectors include vectors derived from lentiviruses such as, but not limited to, HIV-1 and HIV-2. Examples of retroviral vectors include vectors derived from retroviruses such as, but not limited to, Moloney murine leukemia virus (MMLV). Examples of oncoviral vectors include vectors derived from oncoviruses such as, but not limited to, Murine Leukemia Virus (MLV), Spleen Necrosis Virus (SNV), Rous sarcoma virus (RSV) and Avian Leukosis Virus (ALV).

In another aspect, the invention provides a cell comprising a nucleic acid vector, wherein the nucleic acid vector comprises a gene of interest and one or more target sequences for a microRNA within the 3' UTR region of the gene of interest.

In one embodiment, the gene of interest is a human gene. In another embodiment, the gene of interest is a nonhuman gene. In one embodiment, the gene of interest is a p27 gene. In another embodiment, the gene of interest is p53. In other embodiments, the gene of interest is a tumor suppressor gene. A tumor suppressor gene can include, but is not limited to, APC, RBI, INK4, PTEN, MADR2, BRAC1, BRAC2, or DPC4.

In one embodiment, the microRNA is miR-126. In another embodiment, the micro-RNA is miR-143. In another embodiment, the micro-RNA is miR-145. In further embodiments, the microRNA is Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the one or more target sequences comprise SEQ ID NO:2. In another embodiment, the one or more target sequences do not comprise SEQ ID NO:2. In another embodiment, the one or more target sequences comprise a nucleic acid sequence complementary to SEQ ID NO:2. In another embodiment, the one or more target sequences do not comprise a nucleic acid sequence complementary to SEQ ID NO:2.

In one embodiment, the vector comprises four target sequences for a microRNA. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the target sequences for a microRNA are identical. In another embodiment, the target sequences for a microRNA are not identical. The nucleic acid vectors can comprise different combinations of target sequences for various microRNAs, including, but not limited to, miR-126, miR-143, miR-145, Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the target sequences for a microRNA comprise SEQ ID NO:2. In another embodiment, the target sequences for a microRNA do not comprise SEQ ID NO:2. In another embodiment, the target sequences for a microRNA comprise a nucleic acid sequence complementary to SEQ ID NO:2. In another embodiment, the target sequences for a microRNA do not comprise a nucleic acid sequence complementary to SEQ ID NO:2.

In another embodiment, the vector comprises a second gene of interest. In one embodiment, the second gene of interest is a human gene. In another embodiment, the second gene of interest is a non-human gene. In one embodiment, the second gene of interest is p53. In other embodiments, the second gene of interest is a tumor suppressor gene. A tumor suppressor gene can include, but is not limited to, APC, RB1, INK4, PTEN, MADR2, BRAC1, BRAC2, or DPC4. In one embodiment, the second gene of interest is an antithrombotic gene. In another embodiment, the second gene of interest is an anti-inflammatory gene. In another embodiment, the second gene of interest is ENTPD1, TFPI or PTGIS.

In another embodiment, the vector comprises one or more target sequences for a microRNA within the 3' UTR region of the second gene of interest. In one embodiment, the vector comprises one target sequence. In another embodiment, the vector comprises two target sequences. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the nucleic acid vector is a viral vector. In one embodiment, the viral vector is an adenoviral vector. In another embodiment, the viral vector is a lentiviral vector. In one embodiment, the vector is a retroviral vector. In another embodiment, is an oncoviral vector. Examples of adenoviral vectors include vectors derived from adenoviruses such as, but not limited to, adenovirus type 2 (Ad2), adenovirus type 5 (Ad5), adenovirus type 7 (Ad7) and adenovirus type 12 (Ad12). In a further embodiment, the vector is an adeno-associated vector. Examples of adeno-associated vector includes vectors derived from adeno-associated viruses such as, but not limited to, adeno-associated virus type 1 (AAV1), adeno-associated virus type 2 (AAV2), adeno-associated virus type 4 (AAV4), adeno-associated virus type 5 (AAV5), adeno-associated virus type 6 (AAV6), adeno-associated virus type 7 (AAV7), and adeno-associated virus type 2 (AAV2). Examples of lentiviral vectors include vectors derived from lentiviruses such as, but not limited to, HIV-1 and HIV-2. Examples of retroviral vectors include vectors derived from retroviruses such as, but not limited to, Moloney murine leukemia virus (MMLV). Examples of oncoviral vectors include vectors derived from oncoviruses such as, but not limited to, Murine Leukemia Virus (MLV), Spleen Necrosis Virus (SNV), Rous sarcoma virus (RSV) and Avian Leukosis Virus (ALV).

In another embodiment, the cell expresses the microRNA. In another embodiment, the cell does not express the microRNA.

In one embodiment, the gene of interest is not expressed in the cell. In another embodiment, the gene of interest is expressed in the cell. In one embodiment, the second gene of interest is not expressed in the cell. In another embodiment, the second gene of interest is expressed in the cell.

In one embodiment, the cell is an endothelial cell. In another embodiment, the cell is a vascular smooth muscle cell. In further embodiments, the cell may be from the germ line or somatic, totipotent or pluripotent, dividing or non-dividing, parenchyma or epithelium, immortalized or transformed, or the like. The cell may be a stem cell or a differentiated cell. Cell types that are differentiated include, but are not limited to, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine and exocrine glands.

In another embodiment, the cell is a cancer cell. In one embodiment, the cancer is, but is not limited to, breast cancer, lung cancer, kidney cancer, brain cancer, liver cancer, colorectal cancers, progressive lung adenocarcinoma, lymphomas, leukemias, adenocarcinomas and sarcomas.

In other embodiments, the nucleic acid vector is delivered into the cell by any method known to one of skill in the art, such as, but not limited to, injection, transfection, lipofection, microinjection, calcium phosphate or calcium chloride precipitation, DEAE-dextrin-mediated transfection, or electroporation. Electroporation is carried out at approximate voltage and capacitance to result in entry of the DNA construct(s) into cells of interest. Other methods used to transfect cells can also include modified calcium phosphate precipitation, polybrene precipitation, liposome fusion, and receptor-mediated gene delivery.

DNA and Amino Acid Manipulation Methods and Purification Thereof

The present invention utilizes conventional molecular biology, microbiology, and recombinant DNA techniques available to one of ordinary skill in the art. Such techniques are well known to the skilled worker and are explained fully in the literature. See, e.g., Maniatis, Fritsch & Sambrook, "Molecular Cloning: A Laboratory Manual" (1982): "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986): B. Perbal, "A Practical Guide to Molecular Cloning" (1984), and Sambrook, et al., "Molecular Cloning: a Laboratory Manual" (1989).

MicroRNAS

Nucleic acid sequences of various microRNAs, and nucleic acid sequences of various target sequences for microRNAs, are available in the art.

The nucleic acid sequence of miR-126 is depicted in SEQ ID NO: 1.

SEQ ID NO: 1 is a sequence of human miR-126

(residues 1-22) UCGUACCGUGAGUAAUAAUGCG

The nucleic acid sequence of a target sequence of miR-126 is depicted in SEQ ID NO: 2.

SEQ ID NO: 2 is a nucleic acid target sequence of human miR-126 (residues 1-22) CGCATTATTACTCACGGTA

CGA

One of skill in the art can determine the complementary sequence of a nucleic acid target sequence of a microRNA, such as, but not limited to, SEQ ID NO. 2.

Proteins

One skilled in the art can obtain a protein in several ways, which include, but are not limited to, isolating the protein via biochemical means or expressing a nucleotide sequence encoding the protein of interest by genetic engineering methods.

A protein is encoded by a nucleic acid (including, for example, genomic DNA, complementary DNA (cDNA), synthetic DNA, as well as any form of corresponding RNA). For example, it can be encoded by a recombinant nucleic acid of a gene. The proteins of the invention can be obtained from various sources and can be produced according to various techniques known in the art. For example, a nucleic acid that encodes a protein can be obtained by screening DNA libraries, or by amplification from a natural source. A protein can be a fragment or portion thereof. The nucleic acids encoding a protein can be produced via recombinant DNA technology and such recombinant nucleic acids can be prepared by conventional techniques, including chemical synthesis, genetic engineering, enzymatic techniques, or a combination thereof. For example, a p27 protein is the polypeptide encoded by the nucleic acid having the nucleotide sequence show in SEQ ID NO:4. An example of an p27 polypeptide has the amino acid sequence shown in SEQ ID NO: 3.

The polypeptide sequence of human p27 is depicted in SEQ ID NO:3. The nucleotide sequence of human p27 is shown in SEQ ID NO:4. Sequence information related to p27 is accessible in public databases by GenBank Accession numbers NM_004064 (for nucleic acid) and NP_004055 (for protein).

```
SEQ ID NO: 3 is the human wild type amino acid
sequence corresponding to p27 (residues 1-198)
msnvrvsngs pslermdarq aehpkpsacr nlfgpvdhee ltrdlekhcr dmeeasqrkw nfdfqnhkpl egkyewqeve kgslpefyyr pprppkgack vpaqesqdvs gsrpaaplig apansedthl vdpktdpsds qtglaeqcag irkrpatdds stqnkranrt eenvsdgspn agsveqtpkk pglrrrqt SEQ ID NO: 4 is the human wild type nucleic acid
protein sequence corresponding to p27 (residues
1-2413)
   1 cttcttcgtc agcctccctt ccaccgccat attgggccac
     taaaaaaagg gggctcgtct
  61 tttcggggtg tttttctccc cctcccctgt ccccgcttgc
     tcacggctct gcgactccga
 121 cgccggcaag gtttggagag cggctgggtt cgcgggaccc
     gcgggcttgc acccgcccag
 181 actcggacgg gctttgccac cctctccgct tgcctggtcc
     cctctcctct ccgccctccc
 241 gctcgccagt ccatttgatc agcggagact cggcggccgg
     gccggggctt ccccgcagcc
 301 cctgcgcgct cctagagctc gggccgtggc tcgtcgggt
     ctgtgtcttt tggctccgag
 361 ggcagtcgct gggcttccga gaggggttcg ggctgcgtag
     gggcgctttg ttttgttcgg
 421 ttttgttttt ttgagagtgc gagagaggcg gtcgtgcaga
     cccgggagaa agatgtcaaa
 481 cgtgcgagtg tctaacggga gccctagcct ggagcggatg
     gacgccaggc aggcggagca
 541 ccccaagccc tcggcctgca ggaacctctt cggcccggtg
     gaccacgaag agttaacccg
 601 ggacttggag aagcactgca gagacatgga agaggcgagc
     cagcgcaagt ggaatttcga
 661 ttttcagaat cacaaacccc tagagggcaa gtacgagtgg
     caagaggtgg agaagggcag
```

```
 721 cttgcccgag ttctactaca gacccccgcg gccccccaaa
     ggtgcctgca aggtgccggc
 781 gcaggagagc caggatgtca gcgggagccg cccggcggcg
     cctttaattg gggctccggc
 841 taactctgag gacacgcatt tggtggaccc aaagactgat
     ccgtcggaca gccagacggg
 901 gttagcggag caatgcgcag gaataaggaa gcgacctgca
     accgacgatt cttctactca
 961 aaacaaaaga gccaacagaa cagaagaaaa tgtttcagac
     ggttccccaa atgccggttc
1021 tgtggagcag acgcccaaga agcctggcct cagaagacgt
     caaacgtaaa cagctcgaat
1081 taagaatatg tttccttgtt tatcagatac atcactgctt
     gatgaagcaa ggaagatata
1141 catgaaaatt ttaaaaatac atatcgctga cttcatggaa
     tggacatcct gtataagcac
1201 tgaaaaacaa caacacaata acactaaaat tttaggcact
     cttaaatgat ctgcctctaa
1261 aagcgttgga tgtagcatta tgcaattagg ttttttcctta
     tttgcttcat tgtactacct
1321 gtgtatatag ttttttacctt ttatgtagca cataaacttt
     ggggaaggga gggcagggtg
1381 gggctgagga actgacgtgg agcggggtat gaagagcttg
     ctttgattta cagcaagtag
1441 ataaatattt gacttgcatg aagagaagca attttgggga
     agggtttgaa ttgttttctt
1501 taaagatgta atgtcccttt cagagacagc tgatacttca
     tttaaaaaaa tcacaaaaat
1561 ttgaacactg gctaaagata attgctattt attttttacaa
     gaagtttatt ctcatttggg
1621 agatctggtg atctcccaag actatctaaag tttgttagat
     agctgcatgt ggcttttta
1681 aaaaagcaac agaaacctat cctcactgcc ctccccagtc
     tctcttaaag ttggaattta
1741 ccagttaatt actcagcaga atggtgatca ctccaggtag
     tttggggcaa aaatccgagg
1801 tgcttgggag ttttgaatgt taagaattga ccatctgctt
     ttattaaatt tgttgacaaa
1861 attttctcat tttcttttca cttcgggctg tgtaaacaca
     gtcaaaataa ttctaaatcc
```

```
1921  ctcgatattt ttaaagatct gtaagtaact tcacattaaa
      aaatgaaata tttttaatt
1981  taaagcttac tctgtccatt tatccacagg aaagtgttat
      ttttcaagga aggttcagtg
2041  agagaaaagc acacttgtag gataagtgaa atggatacta
      catctttaaa cagtatttca
2101  ttgcctgtgt atggaaaaac catttgaagt gtacctgtgt
      acataactct gtaaaaacac
2161  tgaaaaatta tactaactta tttatgttaa aagatttttt
      ttaatctaga caatatacaa
2221  gccaaagtgg catgttttgt gcatttgtaa atgctgtgtt
      gggtagaata ggttttcccc
2281  tcttttgtta aataatatgg ctatgcttaa aaggttgcat
      actgagccaa gtataatttt
2341  ttgtaatgtg tgaaaaagat gccaattatt gttacacatt
      aagtaatcaa taaagaaaac
2401  ttccatagct att
``` p27 is a protein encoded by the CDKN1B gene. p27 is a cyclin-dependent kinase inhibitor, and is also known as p27Kip1. It is a member of the kinase inhibitor protein (KIP) family. For additional information on p27, see e.g., Nisar P. Malek, Holly Sundberg, Seth McGrew, Keiko Nakayama. Themis R. Kyriakidis & James M. Roberts, 2001, A mouse knock-in model exposes sequential proteolytic pathways that regulate p27Kip1 in Gland S phase, *Nature*, 413, 323-327.

Protein Variants

Protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture.

Techniques for making substitution mutations at predetermined sites in DNA having a known sequence are well known, for example M13 primer mutagenesis and PCR mutagenesis. Amino acid substitutions can be single residues, but can occur at a number of different locations at once. In one non-limiting embodiment, insertions can be on the order of about from 1 to about 10 amino acid residues, while deletions can range from about 1 to about 30 residues. Deletions or insertions can be made in adjacent pairs (for example, a deletion of about 2 residues or insertion of about 2 residues). Substitutions, deletions, insertions, or any combination thereof can be combined to arrive at a final construct. The mutations cannot place the sequence out of reading frame and should not create complementary regions that can produce secondary mRNA structure. Substitutional variants are those in which at least one residue has been removed and a different residue inserted in its place.

Substantial changes in function or immunological identity are made by selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions that can produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or praline is substituted for (or by) any other residue: (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

Minor variations in the amino acid sequences of proteins are provided by the present invention. The variations in the amino acid sequence can be when the sequence maintains at least about 30%, at least about 40%, at least about 50%, at least about 60%, at least about 70%, at least about 75%, at least about 80%, at least about 90%, at least about 95%, or at least about 99% identity to SEQ ID NO: 3, or any other amino acid sequence of interest. For example, conservative amino acid replacements can be utilized. Conservative replacements are those that take place within a family of amino acids that are related in their side chains, wherein the interchangeability of residues have similar side chains.

Genetically encoded amino acids are generally divided into families: (1) acidic amino acids are aspartate, glutamate: (2) basic amino acids are lysine, arginine, histidine; (3) non-polar amino acids are alanine, valine, leucine, isoleucine, praline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, praline, tryptophan, tyrosine and valine. Other families of amino acids include (i) a group of amino acids having aliphatic-hydroxyl sidechains, such as serine and threonine; (ii) a group of amino acids having amide-containing side chains, such as asparagine and glutamine; (iii) a group of amino acids having aliphatic side chains such as glycine, alanine, valine, leucine, and isoleucine; (iv) a group of amino acids having aromatic side chains, such as phenylalanine, tyrosine, and tryptophan; and (v) a group of amino acids having sulfur-containing side chains, such as cysteine and methionine. Useful conservative amino acids substitution groups are: valine-leucine-isoleucine, phenylalanine-tyrosine, lysine-arginine, alanine valine, glutamic-aspartic, and asparagine-glutamine.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gin; Ser, Thr; Lys, Arg; and Phe, Tyr. Substitutional or deletional mutagenesis can be employed to insert sites for N-glycosylation (Asn-X-Thr/Ser) or 0-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Bacterial and Yeast Expression Systems

In bacterial systems, a number of expression vectors can be selected. For example, when a large quantity of a protein encoded by a gene is needed for the induction of antibodies, vectors which direct high level expression of proteins that are readily purified can be used. Non-limiting examples of such vectors include multifunctional *E. coli* cloning and expression vectors such as BLUESCRIPT (Stratagene). pIN vectors or pGEX vectors (Promega, Madison, Wis.) also can be used to express foreign polypeptide molecules as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

Plant and Insect Expression Systems

If plant expression vectors are used, the expression of sequences encoding a protein can be driven by any of a number of promoters. For example, viral promoters such as the 35S and 19S promoters of CaMV can be used alone or in combination with the omega leader sequence from TMV. Alternatively, plant promoters such as the small subunit of RUBISCO or heat shock promoters, can be used. These constructs can be introduced into plant cells by direct DNA transformation or by pathogen-mediated transfection.

An insect system also can be used to express proteins. For example, in one such system *Autographa californica* nuclear polyhedrosis virus (AcNPV) is used as a vector to express foreign genes in *Spodoptera frugiperda* cells or in *Trichoplusia* larvae. Sequences encoding a polypeptide can be cloned into a non-essential region of the virus, such as the polyhedrin gene, and placed under control of the polyhedrin promoter. Successful insertion of nucleic acid sequences, such as a sequence corresponding to a gene of interest, will render the polyhedrin gene inactive and produce recombinant virus lacking coat protein. The recombinant viruses can then be used to infect *S. frugiperda* cells or *Trichoplusia* larvae in which the protein or a variant thereof can be expressed.

Mammalian Expression Systems

An expression vector can include a nucleotide sequence that encodes a polypeptide linked to at least one regulatory sequence in a manner allowing expression of the nucleotide sequence in a host cell. A number of viral-based expression systems can be used to express a protein or a variant thereof in mammalian host cells. For example, if an adenovirus is used as an expression vector, sequences encoding a protein can be ligated into an adenovirus transcription/translation complex comprising the late promoter and tripartite leader sequence. Insertion into a non-essential E1 or E3 region of the viral genome can be used to obtain a viable virus which expresses a protein in infected host cells. Transcription enhancers, such as the Rous sarcoma virus (RSV) enhancer, can also be used to increase expression in mammalian host cells.

Regulatory sequences are well known in the art, and can be selected to direct the expression of a protein or polypeptide of interest in an appropriate host cell as described in Goeddel, *Gene Expression Technology: Methods in Enzymology* 185, Academic Press, San Diego, Calif. (1990). Nonlimiting examples of regulatory sequences include: polyadenylation signals, promoters (such as CMV, ASV, SV40, or other viral promoters such as those derived from bovine papilloma, polyoma, and Adenovirus 2 viruses (Fiers, et al., 1973, *Nature* 273:113; Hager G L, et al., *Curr Opin Genet Dev*, 2002, 12(2):137-41) enhancers, and other expression control elements.

Enhancer regions, which are those sequences found upstream or downstream of the promoter region in noncoding DNA regions, are also known in the art to be important in optimizing expression. If needed, origins of replication from viral sources can be employed, such as if a prokaryotic host is utilized for introduction of plasmid DNA. However, in eukaryotic organisms, chromosome integration is a common mechanism for DNA replication.

Suitable promoters for expressing RNA from a plasmid include, e.g., the U6 or HI RNA pol III promoter sequences, or the cytomegalovirus promoters. Selection of other suitable promoters is within the skill in the art. Recombinant plasmids can comprise inducible or regulatable promoters for expression of the RNA in cells (such as, but not limited to, vascular smooth muscle cells or endothelial cells). For example, a nucleic acid encoding a gene, such as, but not limited to, a p27 gene, and one or more target sequences for a microRNA, such as, but not limited to, miR-126 (comprising one or more sequences of SEQ ID NO: 2) can be placed under the control of the CMV intermediate-early promoter, whereby the nucleic acid sequences encoding the p27 gene are located 3' of the promoter, so that the promoter can initiate transcription of the miRNA gene product coding sequences.

A gene that encodes a selectable marker (for example, resistance to antibiotics or drugs, such as ampicillin, neomycin, G418, and hygromycin) can be introduced into host cells along with the gene of interest in order to identify and select clones that stably express a gene encoding a protein of interest. The gene encoding a selectable marker can be introduced into a host cell on the same plasmid as the gene of interest or can be introduced on a separate plasmid. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein molecule.

For stable transfection of mammalian cells, a small fraction of cells can integrate introduced DNA into their genomes. The expression vector and transfection method utilized can be factors that contribute to a successful integration event. For stable amplification and expression of a desired protein, a vector containing DNA encoding a protein of interest is stably integrated into the genome of eukaryotic cells (for example mammalian cells, such as, but not limited to, vascular smooth muscle cells or endothelial cells), resulting in the stable expression of transfected genes. An exogenous nucleic acid sequence can be introduced into a cell (such as a mammalian cell, either a primary or secondary cell) by homologous recombination as disclosed in U.S. Pat. No. 5,641,670, the contents of which are herein incorporated by reference.

Vectors

Nucleic acid vectors, such as plasmids, suitable for expressing genes of interest and target sequences for microRNAs, methods for inserting nucleic acid sequences into the plasmid to express the gene of interest, and methods of delivering the recombinant vectors to cells of interest are well-established and practiced in the art. See, for example, Zeng et al. (2002), Molecular Cell 9:1327-1333; Tuschl (2002), Nat. Biotechnol, 20:446-448; Brummelkamp et al. (2002). Science 296:550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Genes of interest and target sequences for microRNAs can also be expressed from recombinant viral vectors. The RNA expressed from the recombinant viral vectors can either be isolated from cultured cell expression systems by standard techniques, or can be expressed directly in mammalian cells (for example, vascular smooth muscle cells or endothelial cells). For example, the recombinant viral vectors can comprise sequences that encode the gene of interest and any suitable promoter for expressing the RNA sequences. Vectors can also comprise inducible or regulatable promoters for expression of the gene of interest in cells, such as mammalian cells. As discussed previously, non-limiting examples of suitable promoters include the U6 or HI RNA pol III promoter sequences, or the cytomegalovirus promoters. Selection of other suitable promoters is practiced by those of ordinary skill in the art.

Any viral vector that can harbor the nucleotide sequences for the gene of interest and the one or more target sequences for a microRNA of the invention can be used. Non-limiting examples of such vectors include: vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. For example, AAV vectors can be made to target different cells by engineering the vectors to express different capsid protein serotypes. An AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J. E. et al. (2002), *J Virol* 76:791-801, the entire disclosure of which is herein incorporated by reference.

Recombinant viral vectors suitable for expressing the gene of interest and the one or more target sequences for a microRNA of the invention, methods for inserting nucleic acid sequences for expressing genes of interest in the vector, methods of delivering the viral vector to cells of interest, and recovery of the expressed nucleic acid molecules and proteins are within the skill in the art. See, for example, Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are herein incorporated by reference. Useful viral vectors can be those derived from AV and AAV. A suitable AV vector for expressing a nucleic acid molecule of the invention, a method for constructing the recombinant AV vector, and a method for delivering the vector into target cells, are described in Xia et al. (2002), *Nat. Biotech.* 20:1006-1010, the entire disclosure of which is herein incorporated by reference. Methods for constructing the recombinant AAV vector, and methods for delivering the vectors into target cells are described in Samulski et al. (1987), *J. Virol.* 61:3096-3101; Fisher et al. (1996). *J. Virol.* 70:520-532; Samulski et al. (1989), *J. Virol.* 63:3822-3826; U.S. Pat. Nos. 5,252,479; 5,139,941; International Patent Application No. WO 94/13788: and International Patent Application No. WO 93/24641, the entire disclosures of which are herein incorporated by reference.

Cell Delivery

A eukaryotic expression vector can be used to transfect cells in order to produce proteins encoded by nucleotide sequences of the vector. Mammalian cells (such as, but not limited to, vascular smooth muscle cells or endothelial cells) can contain an expression vector (for example, one that contains a gene encoding a p27 protein or polypeptide) via introducing the expression vector into an appropriate host cell via methods known in the art.

A host cell strain can be chosen for its ability to modulate the expression of the inserted sequences or to process the expressed polypeptide encoded by a gene, such as a p27 gene, in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC: 10801 University Boulevard, Manassas, Va. 20110-2209) and can be chosen to ensure the correct modification and processing of the foreign protein.

An exogenous nucleic acid can be introduced into a cell via a variety of techniques known in the art, such as lipofection, microinjection, calcium phosphate or calcium chloride precipitation. DEAE-dextran-mediated transfection, or electroporation. Electroporation is carried out at approximate voltage and capacitance to result in entry of the DNA construct(s) into cells of interest (such as cells of the end bulb of a hair follicle, for example dermal papilla cells or dermal sheath cells). Other transfection methods also include modified calcium phosphate precipitation, polybrene precipitation, liposome fusion, and receptor-mediated gene delivery.

Cells that will be genetically engineered can be primary and secondary cells obtained from various tissues, and include cell types which can be maintained and propagated in culture. Vertebrate tissue can be obtained by methods known to one skilled in the art, such a punch biopsy or other surgical methods of obtaining a tissue source of the primary cell type of interest. A mixture of primary cells can be obtained from the tissue, using methods readily practiced in the art, such as explanting or enzymatic digestion (for examples using enzymes such as pronase, trypsin, collagenase, elastase dispase, and chymotrypsin). Biopsy methods have also been described in United States Patent Application Publication 2004/0057937 and PCT application publication WO 2001/32840, and are hereby incorporated by reference.

Primary cells can be acquired from the individual to whom the genetically engineered primary or secondary cells are administered. However, primary cells can also be obtained from a donor, other than the recipient, of the same species. The cells can also be obtained from another species (for example, rabbit, cat, mouse, rat, sheep, goat, dog, horse, cow, bird, or pig). Primary cells can also include cells from an isolated vertebrate tissue source grown attached to a tissue culture substrate (for example, flask or dish) or grown in a suspension; cells present in an explant derived from tissue; both of the aforementioned cell types plated for the first time; and cell culture suspensions derived from these plated cells. Secondary cells can be plated primary cells that are removed from the culture substrate and replated, or passaged, in addition to cells from the subsequent passages. Secondary cells can be passaged one or more times. These primary or secondary cells can contain expression vectors having a gene that encodes a protein of interest (for example, a p27 protein or polypeptide).

Delivery of nucleic acids into viable cells can be effected ex vivo, in situ, or in vivo by use of vectors, and more particularly viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (see, for example, Anderson, Nature, supplement to vol. 392, no. 6679, pp. 25-20 (1998)). Introduction of a nucleic acid or a gene encoding a polypeptide of the invention can also be accomplished with extrachromosomal substrates (transient expression) or artificial chromosomes (stable expression). Cells may also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., (1992) *J Gen Virol.* 73(Pt 6):1533-6), adenovirus (Berkner (1992) *Curr Top Microbial Immunol.* 158: 39-66; Berkner (1988) *Biotechniques,* 6(7):616-29; Gorziglia and Kapikian (1992) *J Virol.* 66(7):4407-12; Quantin et al., (1992) *Proc Natl Acad Sci USA.* 89(7):2581-4; Rosenfeld et al., (1992) *Cell.* 68(1):143-55; Wilkinson et al., (1992) *Nucleic Acids Res.* 20(9):2233-9; Stratford-Perricaudet et al., (1990) *Hum Gene Ther.* 1(3):241-56), vaccinia virus (Moss (1992) *Curr Opin Biotechnol.* 3(5):518-22), adeno-associated virus (Muzyczka, (1992) *Curr Top Microbial Immunol.* 158:97-129; Ohi et al., (1990) *Gene.* 89(2): 279-82), herpes-viruses including HSY and EBY (Margolskee (1992) *Curr Top Microbiol Immunol.* 158:67-95; Johnson et al., (1992) *Brain Res Mol Brain Res.* 12(1-3): 95-102: Fink et al., (1992) *Hum Gene Ther.* 3(1):11-9: Breakefield and Geller (1987) *Mol Neurobiol.* 1(4):339-71; Freese et al., (1990) *Biochem Pharmacol.* 40(10):2189-99), and retroviruses of avian (Bandyopadhyay and Temin (1984) *Mol Cell Biol.* 4(4):749-54; Petropoulos et al., (1992) *J Virol.* 66(6):3391-7), murine (Miller et al. (1992) *Mol Cell Biol.* 12(7):3262-72; Miller et al., (1985) *J Virol.* 55(3):521-6; Sorge et al., (1984) *Mol Cell Biol.* 4(9):1730-7; Mann and Baltimore (1985) *J Virol.* 54(2):401-7: Miller et al., (1988) *J Virol.* 62(11):4337-45), and human origin (Shimada et al., (1991) *J Clin Invest.* 88(3): 1043-7; Helseth et al., (1990) *J Virol.* 64(12):6314-8; Page et al., (1990) *J Virol.* 64(11): 5270-6; Buchschacher and Panganiban (1992) *J Virol.* 66(5): 2731-9).

Non-limiting examples of in vivo gene transfer techniques include transfection with viral (typically retroviral) vectors (see U.S. Pat. No. 5,252,479, which is incorporated by reference in its entirety) and viral coat protein-liposome mediated transfection (Dzau et al., Trends in Biotechnology 11:205-210 (1993), incorporated entirely by reference). For example, naked DNA vaccines are generally known in the art; see Brower, Nature Biotechnology, 16:1304-1305 (1998), which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of gene therapy protocols and methods see Anderson et al., Science 256:808-813 (1992); U.S. Pat. Nos. 5,252,479, 5,747,469, 6,017,524, 6,143,290, 6,410,010, 6,511,847; 8,398,968; and 8,404,653 which are all hereby incorporated by reference in their entireties. For an example of gene therapy treatment in humans see Porter et al., NEJM 2011 365:725-733 and Kalas et al. Sci. Transl. Med. 2011. 201 3(95):95. For additional reviews of gene therapy technology, see Friedmann. Science, 244:1275-1281 (1989); Verma, Scientific American: 68-84 (1990); Miller, Nature, 357: 455-460 (1992); Kikuchi et al., J Dermatol Sci. 2008 May; 50(2): 87-98; Isaka et al., Expert Opin Drug Deliv. 2007 September; 4(5):561-71; Jager et al., Curr Gene Ther. 2007 August; 7(4): 272-83; Waehler et al., Nat Rev Genet. 2007 August; 8(8): 573-87; Jensen et al., Ann Med. 2007: 39(2):108-15; Herweijer et al., Gene Ther. 2007 January; 14(2):99-107; Eliyahu et al., Molecules, 2005 Jan. 31; 10(1):34-64; and Altaras et al., Adv Biochem Eng Biotechnol. 2005; 99:193-260, all of which are hereby incorporated by reference in their entireties.

Cell Culturing

Various culturing parameters can be used with respect to the host cell being cultured. Appropriate culture conditions for mammalian cells are well known in the art (Cleveland W L, et al., J Immunol Methods, 1983, 56(2): 221-234) or an be determined by the skilled artisan (see, for example, Ammal Cell Culture: A Practical Approach 2nd Ed., Rickwood, D. and Hames, B. D., eds. (Oxford University Press: New York, 1992)). Cell culturing conditions can vary according to the type of host cell selected. Commercially available medium can be utilized. Non-limiting examples of medium include, for example, Minimal Essential Medium (MEM, Sigma, St. Louis, Mo.): Dulbecco's Modified Eagles Medium (DMEM, Sigma); Ham's FlO Medium (Sigma); HyClone cell culture medium (HyClone, Logan, Utah); RPMI-1640 Medium (Sigma); and chemically-defined (CD) medium, which are formulated for various cell types, e.g., CD-CHO Medium (Invitrogen, Carlsbad, Calif.).

The cell culture media can be supplemented as necessary with supplementary components or ingredients including optional components, in appropriate concentrations or amounts, as necessary or desired. Cell culture medium solutions provide at least one component from one or more of the following categories: (1) an energy source usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that can be required at very low concentrations, usually in the micromolar range.

The medium also can be supplemented electively with one or more components from any of the following categories: (1) salts, for example, magnesium, calcium, and phosphate: (2) hormones and other growth factors such as, serum, insulin, transferrin, and epidermal growth factor: (3) protein and tissue hydrolysates, for example peptone or peptone mixtures which can be obtained from purified gelatin, plant material, or animal byproducts; (4) nucleosides and bases such as, adenosine, thymidine, and hypoxanthine; (5) buffers: such as HEPES: (6) antibiotics, such as gentamycin or ampicillin; (7) cell protective agents, for example pluronic polyol; and (8) galactose. In one embodiment, soluble factors can be added to the culturing medium.

The mammalian cell culture that can be used with the present invention is prepared in a medium suitable for the type of cell being cultured. In one embodiment, the cell culture medium can be any one of those previously discussed (for example, MEM) that is supplemented with serum from a mammalian source (for example, fetal bovine serum (FBS)). In another embodiment, the medium can be a conditioned medium to sustain the growth of mammalian cells. In other embodiments of the invention, cells are grown in a suspension culture (for example, a three-dimensional culture such as a hanging drop culture) in the presence of an effective amount of enzyme, wherein the enzyme substrate is an extracellular matrix molecule in the suspension culture. For example, the enzyme can be a hyaluronidase.

A suspension culture is a type of culture wherein cells, or aggregates of cells multiply while suspended in liquid medium. A suspension culture comprising mammalian cells can be used for the maintenance of cell types that do not adhere or to enable cells to manifest specific cellular characteristics that are not seen in the adherent form. Some types of suspension cultures can include three-dimensional cultures or a hanging drop culture. A hanging-drop culture is a culture in which the material to be cultivated is inoculated into a drop of fluid attached to a flat surface (such as a cover glass, glass slide, Petri dish, flask, and the like), and can be inverted over a hollow surface. Cells in a hanging drop can aggregate toward the hanging center of a drop as a result of gravity. However, according to the methods of the invention cells cultured in the presence of a protein that degrades the extracellular matrix (such as collagenase, chondroitinase, hyaluronidase, and the like) will become more compact and aggregated within the hanging drop culture, for degradation of the ECM will allow cells to become closer in proximity to one another since less of the ECM will be present. See also International PCT Publication No. WO2007/100870, which is incorporated by reference.

Three-dimensional cultures can be formed from agar (such as Gey's Agar), hydrogels (such as matrigel, agarose, and the like; Lee et al., (2004) *Biomaterials* 25: 2461-2466) or polymers that are cross-linked. These polymers can comprise natural polymers and their derivatives, synthetic polymers and their derivatives, or a combination thereof. Natural polymers can be anionic polymers, cationic polymers, amphipathic polymers, or neutral polymers. Non-limiting examples of anionic polymers can include hyaluronic acid, alginic acid (alginate), carageenan, chondroitin sulfate, dextra sulfate, and pectin. Some examples of cationic polymers, include but are not limited to, chitosan or polylysine. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73). Examples of amphipathicyolymers can include, but are not limited to collagen, gelatin, fibrin, and carboxymethyl chitin. Non-limiting examples of neutral polymers can include dextran, agarose, or pullulan. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73).

Cells suitable for culturing according to methods of the invention can harbor introduced expression vectors such as plasmids. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 2001, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

Obtaining and Purifying Polypeptides

A polypeptide molecule encoded by a gene, such as a p27 gene, or a variant thereof, can be obtained by purification from human cells expressing a protein or polypeptide encoded by a p27 gene via in vitro or in vivo expression of a nucleic acid sequence encoding a p27 protein or polypeptide: or by direct chemical synthesis.

Detecting Polypeptide Expression

Host cells which contain a nucleic acid encoding a p27 protein or polypeptide, and which subsequently express a protein encoded by a p27 gene, can be identified by various procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a nucleic acid encoding a p27 protein or polypeptide can be detected by DNA-DNA or DNA-RNA hybridization or amplification using probes or fragments of nucleic acids encoding a p27 protein or polypeptide. In one embodiment, a fragment of a nucleic acid of a p27 gene can encompass any portion of at least about 8 consecutive nucleotides of SEQ ID NO: 4. In another embodiment, the fragment can comprise at least about 10 consecutive nucleotides, at least about 15 consecutive nucleotides, at least about 20 consecutive nucleotides, or at least about 30 consecutive nucleotides of SEQ ID NO: 4. Fragments can include all possible nucleotide lengths between about 8 and about 100 nucleotides, for example, lengths between about 15 and about 100 nucleotides, or between about 20 and about 100 nucleotides. Nucleic acid amplification-based assays involve the use of oligonucleotides selected from sequences encoding a polypeptide encoded by a p27 gene to detect transformants which contain a nucleic acid encoding a p27 protein or polypeptide.

Protocols for detecting and measuring the expression of a polypeptide encoded by a gene, such as a p27 gene, using either polyclonal or monoclonal antibodies specific for the polypeptide are well established. Non-limiting examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a polypeptide encoded by a gene, such as a p27 gene, can be used, or a competitive binding assay can be employed.

Labeling and conjugation techniques are known by those skilled in the art and can be used in various nucleic acid and amino acid assays. Methods for producing labeled hybridization or PCR probes for detecting sequences related to nucleic acid sequences encoding a protein, such as, but not limited to, p27, include, but are not limited to, oligo labeling, nick translation, end-labeling, or PCR amplification using a labeled nucleotide. Alternatively, nucleic acid sequences encoding a polypeptide encoded by a gene, such as a p27 gene, can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, and/or magnetic particles.

Expression and Purification of Polypeptides

Host cells transformed with a nucleic acid sequence encoding a polypeptide, such as, but not limited to, p27, can be cultured under conditions suitable for the expression and recovery of the protein from cell culture. The polypeptide produced by a transformed cell can be secreted or contained intracellularly depending on the sequence and/or the vector used. Expression vectors containing a nucleic acid sequence encoding a polypeptide, such as, but not limited to, p27, can be designed to contain signal sequences which direct secretion of soluble polypeptide molecules encoded by a gene, such as, but not limited to, p27, or a variant thereof, through a prokaryotic or eukaryotic cell membrane or which direct the membrane insertion of membrane-bound a polypeptide molecule encoded by a p27 gene or a variant thereof.

Other constructions can also be used to join a gene sequence encoding a polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Including cleavable linker sequences (i.e., those specific for Factor Xa or enterokinase (Invitrogen, San Diego, Calif.)) between the purification domain and a polypeptide encoded by a p27 gene, for example, also can be used to facilitate purification. One such expression vector provides for expression of a fusion protein containing a polypeptide encoded by a p27 gene, for example, and 6 histidine residues (SEQ ID NO: 5) preceding a thioredoxin or an enterokinase cleavage site. The histidine residues facilitate purification by immobilized metal ion affinity chromatography, while the enterokinase cleavage site provides a means for purifying the polypeptide encoded by a p27 gene.

A p27 polypeptide can be purified from any human or non-human cell which expresses the polypeptide, including those which have been transfected with expression constructs that express a p27 protein. A purified p27 protein can be separated from other compounds which normally associate with a protein encoded by a p27 gene in the cell, such as certain proteins, carbohydrates, or lipids, using methods practiced in the art. Non-limiting methods include size exclusion chromatography, ammonium sulfate fractionation, ion exchange chromatography, affinity chromatography, and preparative gel electrophoresis.

Chemical Synthesis

Nucleic acid sequences comprising a gene, such as, but not limited to, a p27 gene, that encodes a polypeptide can be synthesized, in whole or in part, using chemical methods known in the art. Alternatively, a polypeptide, such as, but not limited to, p27, can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of p27 polypeptides can be separately synthesized and combined using chemical methods to produce a full-length molecule. In one embodiment, a fragment of a nucleic acid sequence that comprises a p27 gene can encompass any portion of at least about 8 consecutive nucleotides of SEQ ID NO: 4. In one embodiment, the fragment can comprise at least about 10 nucleotides, at least about 15 nucleotides, at least about 20 nucleotides, or at least about 30 nucleotides of SEQ ID NO: 4. Fragments include all possible nucleotide lengths between about 8 and about 100 nucleotides, for example, lengths between about 15 and about 100 nucleotides, or between about 20 and about 100 nucleotides.

Other nucleic acid sequences, such as, but not limited to, microRNA target sequences, can be synthesized, in whole or in part, using chemical methods known in the art. Automated synthesis can be achieved, for example, using Applied Biosystems 431A Peptide Synthesizer (Perkin Elmer). In one embodiment, a fragment of a nucleic acid sequence that comprises microRNA target sequences can encompass any portion of at least about 4 consecutive nucleotides of SEQ ID NO: 2, or any nucleic acid sequence complementary to SEQ ID NO: 2. In one embodiment, the fragment can comprise at least about 6 nucleotides, at least about 8 nucleotides, at least about 10 nucleotides, or at least about 12 nucleotides, at least about 14 nucleotides, at least about 16 nucleotides of SEQ ID NO: 2, or any nucleic acid sequence complementary to SEQ ID NO: 2. Fragments include all possible nucleotide lengths between about 4 and about 40 nucleotides, for example, lengths between about 10 and about 30 nucleotides, or between about 10 and about 20 nucleotides.

In another embodiment, a fragment of a nucleic acid sequence that comprises microRNA target sequences can encompass one or more nucleic acid sequences of SEQ ID NO: 2, or any nucleic acid sequence complementary to SEQ ID NO: 2. In one embodiment, a fragment of a nucleic acid sequence that comprises microRNA target sequences encompasses one nucleic acid sequence of SEQ ID NO: 2, or any nucleic acid sequence complementary to SEQ ID NO. 2. In another embodiment, a fragment of a nucleic acid sequence that comprises microRNA target sequences encompasses two nucleic acid sequence of SEQ ID NO: 2, or any nucleic acid sequence complementary to SEQ ID NO. 2. In one embodiment, a fragment of a nucleic acid sequence that comprises microRNA target sequences encompasses three nucleic acid sequence of SEQ ID NO: 2, or any nucleic acid sequence complementary to SEQ ID NO. 2. In another embodiment, a fragment of a nucleic acid sequence that comprises microRNA target sequences encompasses four nucleic acid sequence of SEQ ID NO: 2, or any nucleic acid sequence complementary to SEQ ID NO. 2. In other embodiments, a fragment of a nucleic acid sequence that comprises microRNA target sequences encompasses 5, 6, 7, 8, 9, 10, or more nucleic acid sequences of SEQ ID NO: 2, or any nucleic acid sequence complementary to SEQ ID NO. 2.

A synthetic peptide can be substantially purified via high performance liquid chromatography (HPLC). The composition of a synthetic polypeptide of can be confirmed by amino acid analysis or sequencing. Additionally, any portion of an amino acid sequence comprising a protein encoded by a gene can be altered during direct synthesis and/or combined using chemical methods with sequences from other proteins to produce a variant polypeptide or a fusion protein.

Pharmaceutical Compositions

In another aspect, the present invention provides for a composition comprising a nucleic acid vector, wherein the nucleic acid vector comprises a gene of interest and one or more target sequences for a microRNA within the 3' UTR region of the gene of interest. In one embodiment, the composition is a pharmaceutical composition.

In one embodiment, the gene of interest is a human gene. In another embodiment, the gene of interest is a non-human gene. In one embodiment, the gene of interest is a p27 gene. In another embodiment, the gene of interest is p53. In other embodiments, the gene of interest is a tumor suppressor gene. A tumor suppressor gene can include, but is not limited to, APC, RBI, INK4, PTEN, MADR2, BRAC1, BRAC2, or DPC4.

In one embodiment, the microRNA is miR-126. In another embodiment, the micro-RNA is miR-143. In another embodiment, the micro-RNA is miR-145. In further embodiments, the microRNA is Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the one or more target sequences comprise SEQ ID NO:2. In another embodiment, the one or more target sequences do not comprise SEQ ID NO:2. In another embodiment, the one or more target sequences comprise a nucleic acid sequence complementary to SEQ ID NO:2. In another embodiment, the one or more target sequences do not comprise a nucleic acid sequence complementary to SEQ ID NO:2.

In one embodiment, the vector comprises four target sequences for a microRNA. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the target sequences for a microRNA are identical. In another embodiment, the target sequences for a microRNA are not identical. The nucleic acid vectors can comprise different combinations of target sequences for various microRNAs, including, but not limited to, miR-126, miR-143, miR-145, Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the target sequences for a microRNA comprise SEQ ID NO:2. In another embodiment, the target sequences for a microRNA do not comprise SEQ ID NO:2. In another embodiment, the target sequences for a microRNA comprise a nucleic acid sequence complementary to SEQ ID NO:2. In another embodiment, the target sequences for a microRNA do not comprise a nucleic acid sequence complementary to SEQ ID NO:2

In another embodiment, the vector comprises a second gene of interest. In one embodiment, the second gene of interest is a human gene. In another embodiment, the second gene of interest is a non-human gene. In one embodiment, the second gene of interest is p53. In other embodiments, the second gene of interest is a tumor suppressor gene. A tumor suppressor gene can include, but is not limited to, APC, RB1, INK4, PTEN, MADR2, BRAC1, BRAC2, or DPC4. In one embodiment, the second gene of interest is an antithrombotic gene. In another embodiment, the second gene of interest is an anti-inflammatory gene. In another embodiment, the second gene of interest is ENTPD1, TFPI or PTGIS.

In another embodiment, the vector comprises one or more target sequences for a microRNA within the 3' UTR region of the second gene of interest. In one embodiment, the vector comprises one target sequence. In another embodiment, the vector comprises two target sequences. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the nucleic acid vector is a viral vector. In one embodiment, the viral vector is an adenoviral vector. In another embodiment, the viral vector is a lentiviral vector. In one embodiment, the vector is a retroviral vector. In another embodiment, is an oncoviral vector. Examples of adenoviral vectors include vectors derived from adenoviruses such as, but not limited to, adenovirus type 2 (Ad2), adenovirus type 5 (Ad5), adenovirus type 7 (Ad7) and adenovirus type 12 (Ad12). In a further embodiment, the vector is an adeno-associated vector. Examples of adeno-associated vector includes vectors derived from adeno-associated viruses such as, but not limited to, adeno-associated virus type 1 (AAV1), adeno-associated virus type 2 (AAV2), adeno-associated virus type 4 (AAV4), adeno-associated virus type 5 (AAV5), adeno-associated virus type 6 (AAV6), adeno-associated virus type 7 (AAV7), and adeno-associated virus type 2 (AAV2). Examples of lentiviral vectors include vectors derived from lentiviruses such as, but not limited to, HIV-1 and HIV-2. Examples of retroviral vectors include vectors derived from retroviruses such as, but not limited to, Moloney murine leukemia virus (MMLV). Examples of oncoviral vectors include vectors derived from oncoviruses such as, but not limited to, Murine Leukemia Virus (MLV), Spleen Necrosis Virus (SNV), Rous sarcoma virus (RSV) and Avian Leukosis Virus (ALV).

Methods of Treatment

In yet another aspect, the invention provides a method of treating or preventing a cardiovascular disease in a subject in need thereof, the method comprising administering a nucleic acid vector to the subject, wherein the nucleic acid vector comprises a gene of interest and one or more target sequences for a microRNA within the 3' UTR region of the gene of interest.

In one embodiment, the gene of interest is a human gene. In another embodiment, the gene of interest is a nonhuman gene. In one embodiment, the gene of interest is a p27 gene. In another embodiment, the gene of interest is p53. In other embodiments, the gene of interest is a tumor suppressor gene. A tumor suppressor gene can include, but is not limited to, APC, RBI, INK4, PTEN, MADR2, BRAC1, BRAC2, or DPC4.

In one embodiment, the microRNA is miR-126. In another embodiment, the micro-RNA is miR-143. In another embodiment, the micro-RNA is miR-145. In further embodiments, the microRNA is Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the one or more target sequences comprise SEQ ID NO:2. In another embodiment, the one or more target sequences do not comprise SEQ ID NO:2. In another embodiment, the one or more target sequences comprise a nucleic acid sequence complementary to SEQ ID NO:2. In another embodiment, the one or more target sequences do not comprise a nucleic acid sequence complementary to SEQ ID NO:2.

In one embodiment, the vector comprises four target sequences for a microRNA. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the target sequences for a microRNA are identical. In another embodiment, the target sequences for a microRNA are not identical. The nucleic acid vectors can comprise different combinations of target sequences for various microRNAs, including, but not limited to, miR-126, miR-143, miR-145, Let7-f, miR-27b, miR-130a, miR-221, miR-222, miR-17, miR-18a, miR-19a, miR-20a, miR-19b, miR-92a, miR-378, miR-210, miR-15, miR-16, miR-20b, miR-155, or miR-21.

In one embodiment, the target sequences for a microRNA comprise SEQ ID NO:2. In another embodiment, the target sequences for a microRNA do not comprise SEQ ID NO:2. In another embodiment, the target sequences for a microRNA comprise a nucleic acid sequence complementary to SEQ ID NO:2. In another embodiment, the target sequences for a microRNA do not comprise a nucleic acid sequence complementary to SEQ ID NO:2.

In another embodiment, the vector comprises a second gene of interest. In one embodiment, the second gene of interest is a human gene. In another embodiment, the second gene of interest is a non-human gene. In one embodiment, the second gene of interest is p53. In other embodiments, the second gene of interest is a tumor suppressor gene. A tumor suppressor gene can include, but is not limited to, APC, RB 1, INK4, PTEN, MADR2, BRAC1. BRAC2, or DPC4. In one embodiment, the second gene of interest is an anti-thrombotic gene. In another embodiment, the second gene of interest is an anti-inflammatory gene. In another embodiment, the second gene of interest is ENTPD1, TFPI or PTGIS.

In another embodiment, the vector comprises one or more target sequences for a microRNA within the 3' UTR region of the second gene of interest. In one embodiment, the vector comprises one target sequence. In another embodiment, the vector comprises two target sequences. In another embodiment, the vector comprises three target sequences. In another embodiment, the vector comprises four target sequences. In another embodiment, the vector comprises five target sequences. In another embodiment, the vector comprises six target sequences. In another embodiment, the vector comprises seven target sequences. In another embodiment, the vector comprises eight target sequences. In other embodiments, the vector comprises nine, ten, eleven, twelve, thirteen, fourteen, fifteen, or more target sequences.

In one embodiment, the nucleic acid vector is a viral vector. In one embodiment, the viral vector is an adenoviral vector. In another embodiment, the viral vector is a lentiviral vector. In one embodiment, the vector is a retroviral vector. In another embodiment, is an oncoviral vector. Examples of adenoviral vectors include vectors derived from adenoviruses such as, but not limited to, adenovirus type 2 (Ad2), adenovirus type 5 (Ad5), adenovirus type 7 (Ad7) and adenovirus type 12 (Ad12). In a further embodiment, the vector is an adeno-associated vector. Examples of adeno-associated vector includes vectors derived from adeno-associated viruses such as, but not limited to, adeno-associated virus type 1 (AAV1), adeno-associated virus type 2 (AAV2), adeno-associated virus type 4 (AAV4), adeno-associated virus type 5 (AAV5), adeno-associated virus type 6 (AAV6), adeno-associated virus type 7 (AAV7), and adeno-associated virus type 2 (AAV2). Examples of lentiviral vectors include vectors derived from lentiviruses such as, but not limited to, HIV-1 and HIV-2. Examples of retroviral vectors include vectors derived from retroviruses such as, but not limited to, Moloney murine leukemia virus (MMLV). Examples of oncoviral vectors include vectors derived from oncoviruses such as, but not limited to, Murine Leukemia Virus (MLV), Spleen Necrosis Virus (SNV), Rous sarcoma virus (RSV) and Avian Leukosis Virus (ALV).

In one embodiment, the nucleic acid vector is delivered into a cell of the subject. Delivery can be conducted by any method known to one of skill in the art, including, but not limited to, injection, transfection, lipofection, microinjection, calcium phosphate or calcium chloride precipitation, DEAE-dextrin-mediated transfection, or electroporation. Electroporation is carried out at approximate voltage and capacitance to result in entry of the DNA construct(s) into cells of interest. Other methods used to transfect cells can also include modified calcium phosphate precipitation, polybrene precipitation, liposome fusion, and receptor-mediated gene delivery.

In another embodiment, the cell expresses the microRNA. In another embodiment, the cell does not express the microRNA.

In one embodiment, the gene of interest is not expressed in the cell. In another embodiment, the gene of interest is expressed in the cell. In one embodiment, the second gene of interest is not expressed in the cell. In another embodiment, the second gene of interest is expressed in the cell.

In one embodiment, the cell is an endothelial cell. In another embodiment, the cell is a vascular smooth muscle cell. In further embodiments, the cell may be from the germ line or somatic, totipotent or pluripotent, dividing or non-dividing, parenchyma or epithelium, immortalized or transformed, or the like. The cell may be a stem cell or a differentiated cell. Cell types that are differentiated include, but are not limited to, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine and exocrine glands.

In another embodiment, the cell is a cancer cell. The cancer can be, but is not limited to, breast cancer, lung cancer, kidney cancer, brain cancer, liver cancer, colorectal cancers, progressive lung adenocarcinoma, lymphomas, leukemias, adenocarcinomas and sarcomas.

In one embodiment, the cardiovascular disease is coronary artery disease. In another embodiment, the cardiovascular disease is atherosclerotic coronary artery disease. In further embodiments, the cardiovascular disease includes, but is not limited to, coronary vasospasm, restenosis, myocardial ischemia, stent induced injury, stent thrombosis, cardiomyopathy, hypertensive heart disease, heart failure, corpulmonale, cardiac dysrhythmias, inflammatory heart disease, valvular heart disease, peripheral arterial disease, cerebrovascular disease, congenital heart disease, atherosclerosis, arterial injury and rheumatic heart disease. The methods of the invention can also be used for other vascular conditions, such as vascular access failure, for example, in hemodialysis.

Pharmaceutical Compositions and Administration for Therapy

Nucleic acid vectors of the invention can be administered to the subject once (e.g., as a single injection or deposition). Alternatively, nucleic acid vectors of the invention can be administered once or twice daily to a subject in need thereof for a period of from about two to about twenty-eight days, or from about seven to about ten days. Nucleic acid vectors of the invention can also be administered once or twice daily to a subject for a period of 1, 2, 3, 4, 5, 6, 7, 8, 9, 10, 11, 12 times per year, or a combination thereof. Furthermore, nucleic acid vectors of the invention can be co-administrated with another therapeutic. Where a dosage regimen comprises multiple administrations, the effective amount of the nucleic acid vectors administered to the subject can comprise the total amount of the nucleic acid vectors administered over the entire dosage regimen.

Nucleic acid vectors of the invention can be administered to a subject by any means suitable for delivering the nucleic acid vectors to cells of the subject. For example, nucleic acid vectors can be administered by methods suitable to transfect cells. Transfection methods for eukaryotic cells are well known in the art, and include direct injection of a nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The nucleic acid vectors of the invention may be administered to a subject in an amount effective to treat or prevent a cardiovascular disease, such as, but not limited to, coronary artery disease. One of skill in the art can readily determine what will be an effective amount of the nucleic acid vectors of the invention to be administered to a subject, taking into account whether the nucleic acid vectors are being used prophylactically or therapeutically, and taking into account other factors such as the age, weight and sex of the subject, any other drugs that the subject may betaking, any allergies or contraindications that the subject may have, and the like. For example, an effective amount can be determined by the skilled artisan using known procedures, including analysis of titration curves established in vitro or in vivo. Also, one of skill in the art can determine the effective dose from performing pilot experiments in suitable animal model species and scaling the doses up or down depending on the subjects weight etc. Effective amounts can also be determined by performing clinical trials in individuals of the same species as the subject, for example starting at a low dose and gradually increasing the dose and monitoring the effects on a metabolic disorder, or coronary artery disease. Appropriate dosing regimens can also be determined by one of skill in the art without undue experimentation, in order to determine, for example, whether to administer the agent in one single dose or in multiple doses, and in the case of multiple doses, to determine an effective interval between doses.

A therapeutically effective dose of a nucleic acid vector of the invention that treats or prevents a cardiovascular disease, such as, but not limited to, coronary artery disease, can depend upon a number of factors known to those of ordinary skill in the art. The dose(s) of the nucleic acid vectors can vary, for example, depending upon the identity, size, and condition of the subject or sample being treated, further depending upon the route by which the composition comprising nucleic acid vectors is to be administered, if applicable, and the effect which the practitioner desires the nucleic acid vectors to have upon the target of interest. These amounts can be readily determined by a skilled artisan. Any of the therapeutic applications described herein can be applied to any subject in need of such therapy, including, for example, a mammal such as a dog, a cat, a cow, a horse, a rabbit, a monkey, a pig, a sheep, a goat, or a human.

The compositions of this invention can be formulated and administered to reduce the symptoms associated with a cardiovascular disease, such as, but not limited to, coronary artery disease, by any means that produces contact of the active ingredient with the agent's site of action in the body of a subject, such as a human or animal (e.g., a dog, cat, or horse). They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic or localized administration. Techniques and formulations generally can be found in *Remington's Pharmaceutical Sciences*, Meade Publishing Co., Easton, Pa. (20$^{th}$ Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active ingredient can be used. Supplementary active compounds can also be incorporated into the compositions.

The invention also provides for a kit that comprises a pharmaceutically acceptable carrier and one or more nucleic acid vector(s) of the invention packaged with instructions for use.

A pharmaceutical composition containing nucleic acid vectors of the invention can be administered in conjunction with a pharmaceutically acceptable carrier, for any of the therapeutic effects discussed herein. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of injectable compositions can be brought about by incorporating an agent which delays absorption, for example, aluminum monostearate and gelatin.

Sterile injectable solutions can be prepared by incorporating the nucleic acid vectors of the invention in the required amount in an appropriate solvent with one or a combination of ingredients enumerated herein, as required, followed by filtered sterilization. Generally, dispersions are prepared by incorporating the nucleic acid vectors into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the nucleic acid vectors are formulated into ointments, salves, gels, or creams as generally known in the art. In some embodiments, the nucleic acid vectors can be applied via transdermal delivery systems, which slowly releases the nucleic acid vectors for percutaneous absorption. Permeation enhancers can be used to facilitate transdermal penetration of the active factors in the conditioned media. Transdermal patches are described in for example, U.S. Pat. Nos. 5,407,713; 5,352,456; 5,332, 213; 5,336,168; 5,290,561; 5,254,346; 5,164,189; 5,164, 189; 5,163,899; 5,088,977; 5,087,240; 5,008,110; and 4,921, 475.

Administration of the nucleic acid vectors is not restricted to a single route, but may encompass administration by multiple routes. For instance, exemplary administrations by multiple routes include, among others, a combination of intradermal and intramuscular administration, or intradermal and subcutaneous administration. Multiple administrations may be sequential or concurrent. Other modes of application by multiple routes will be apparent to the skilled artisan.

The nucleic acid vectors of the invention may be formulated into compositions for administration to subjects for the treatment and/or prevention of a cardiovascular disease, such as, but not limited to, coronary artery disease. Such compositions may comprise the nucleic acid vectors of the invention in admixture with one or more pharmaceutically acceptable diluents and/or carriers and optionally one or more other pharmaceutically acceptable additives. The pharmaceutically-acceptable diluents and/or carriers and any other additives must be "acceptable" in the sense of being compatible with the other ingredients of the composition and not deleterious to the subject to whom the composition will be administered. One of skill in the art can readily formulate the nucleic acid vectors of the invention into compositions suitable for administration to subjects, such as human subjects, for example using the teaching a standard text such as Remington's Pharmaceutical Sciences, 18th ed, (Mack Publishing Company: Easton, Pa., 1990), pp. 1635-36), and by taking into account the selected route of delivery.

Examples of diluents and/or carriers and/or other additives that may be used include, but are not limited to, water, glycols, oils, alcohols, aqueous solvents, organic solvents, DMSO, saline solutions, physiological buffer solutions, peptide carriers, starches, sugars, preservatives, antioxidants, coloring agents, pH buffering agents, granulating agents, lubricants, binders, disintegrating agents, emulsifiers, binders, excipients, extenders, glidants, solubilizers, stabilizers, surface active agents, suspending agents, tonicity agents, viscosity-altering agents, carboxymethyl cellulose, crystalline cellulose, glycerin, gum arabic, lactose, magnesium stearate, methyl cellulose, powders, saline, sodium alginate. The combination of diluents and/or carriers and/or other additives used can be varied taking into account the nature of the active agents used (for example the solubility and stability of the active agents), the route of delivery (e.g. oral, parenteral, etc.), whether the agents are to be delivered over an extended period (such as from a controlled-release capsule), whether the agents are to be co-administered with other agents, and various other factors. One of skill in the art will readily be able to formulate the nucleic acid vectors for the desired use without undue experimentation.

The compositions of the invention may be administered to a subject by any suitable method that allows the agent to exert its effect on the subject in vivo. For example, the compositions may be administered to the subject by known procedures including, but not limited to, by oral administration, sublingual or buccal administration, parenteral administration, transdermal administration, via inhalation, via nasal delivery, vaginally, rectally, and intramuscularly. The compositions of the invention may be administered parenterally, or by epifascial, intracapsular, intracutaneous, subcutaneous, intradermal, intrathecal, intramuscular, intraperitoneal, intrasternal, intravascular, intravenous, parenchymatous, or sublingual delivery. Delivery may be by injection, infusion, catheter delivery, or some other means, such as by tablet or spray. In one embodiment, the nucleic acid vectors of the invention are administered to the subject by way of delivery directly to the heart tissue, such as by way of a catheter inserted into, or in the proximity of the subject's heart, or by using delivery vehicles capable of targeting the drug to the heart. For example, the nucleic acid vectors of the invention may be conjugated to or administered in conjunction with an agent that is targeted to the heart, such as an antibody or antibody fragment. In one embodiment, the nucleic acid vectors of the invention are administered to the subject by way of delivery directly to the tissue of interest, such as by way of a catheter inserted into, or in the proximity of the subject's tissue of interest, or by using delivery vehicles capable of targeting the nucleic acid vectors to the muscle, such as an antibody or antibody fragment.

For oral administration, a formulation of the nucleic acid vectors of the invention may be presented as capsules, tablets, powders, granules, or as a suspension or solution. The formulation may contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration by through a route other than the alimentary canal), the nucleic acid vectors of the invention may be combined with a sterile aqueous solution that is isotonic with the blood of the subject. Such a formulation may be prepared by dissolving the active ingredient in water containing physiologically-compatible substances, such as sodium chloride, glycine and the like, and having a buffered pH compatible with physiological conditions, so as to produce an aqueous solution, then rendering the solution sterile. The formulation may be presented in unit or multi-dose containers, such as sealed ampoules or vials. The formulation may be delivered by injection, infusion, or other means known in the art.

For transdermal administration, the nucleic acid vectors of the invention may be combined with skin penetration enhancers, such as propylene glycol, polyethylene glycol, isopropanol, ethanol, oleic acid, N-methylpyrrolidone and the like, which increase the permeability of the skin to the nucleic acid vectors of the invention and permit the nucleic acid vectors to penetrate through the skin and into the bloodstream. The nucleic acid vectors of the invention also may be further combined with a polymeric substance, such as ethyl-cellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the nucleic acid vectors of the invention are provided in unit dose form such as a tablet, capsule or single-dose injection or infusion vial.

Combination Therapy

According to the methods of the invention, a nucleic acid vector of the invention can be administered to a subject either as a single agent, or in combination with one or more other agents. In one embodiment, a nucleic acid vector of the invention is administered to a subject as a single agent. In one embodiment, a nucleic acid vector of the invention is administered to a subject alone. In one embodiment, a nucleic acid vector of the invention is administered to a subject in combination with one or more other agents.

In certain embodiments, a nucleic acid vector of the invention may be used in combination with other agents that are used for the treatment or prevention of a cardiovascular disease, such as, but not limited to, coronary artery disease in a subject. In certain embodiments, a nucleic acid vector of the invention may be used in combination with other agents that are not used for the treatment or prevention of a cardiovascular disease, such as, but not limited to, coronary artery disease in a subject. In one embodiment, a nucleic acid vector of the invention may be delivered to a subject as part of the same pharmaceutical composition or formulation containing one or more additional active agents. In another embodiment, a nucleic acid vector of the invention may be delivered to a subject in a composition or formulation containing only that active agent, while one or more other agents are administered to the subject in one or more separate compositions or formulations. In one embodiment, the other agents are not used for the treatment or prevention of a cardiovascular disease, such as, but not limited to, coronary artery disease in a subject. In another embodiment, the other agents are used for the treatment or prevention of a cardiovascular disease, such as, but not limited to, coronary artery disease in a subject.

A nucleic acid vector of the invention and the other agents that are used for the treatment or prevention of a cardiovascular disease, such as, but not limited to, coronary artery disease in a subject, may be administered to the subject at the same time, or at different times. A nucleic acid vector of the invention and the other agents that are not used for the treatment or prevention of a cardiovascular disease, such as, but not limited to, coronary artery disease, may be administered to the subject at the same time, or at different times. For example, a nucleic acid vector of the invention and the other agents may be administered within minutes, hours, days, weeks, or months of each other, for example as part of the overall treatment regimen of a subject. In some embodiments, a nucleic acid vector of the invention may be administered prior to the administration of other agents. In other embodiments, a nucleic acid vector of the invention may be administered subsequent to the administration of other agents.

In some embodiments, the administration of a nucleic acid vector of the invention in combination with one or more other agents has an additive effect, in comparison with administration of the nucleic acid vector of the invention alone, or administration of the one or more other agents alone. In other embodiments, the administration of a nucleic acid vector of the invention in combination with one or more other agents has a synergistic effect, in comparison with administration of the nucleic acid vector of the invention alone, or administration of the one or more other agents alone. In some embodiments, the administration of a nucleic acid vector of the invention in combination with one or more other agents can help reduce side effects, in comparison with administration of the nucleic acid vector of the invention alone, or administration of the one or more other agents alone.

In some embodiments, the nucleic acid vector of the invention is used as an adjuvant therapy. In other embodiments, the nucleic acid vector of the invention is used in combination with an adjuvant therapy.

The invention may also be used in combination with known therapies for a cardiovascular disease. Examples include, but are not limited to, aspirin; statins, such as atorvastatin (Lipitor, Torvast), fluvastatin (Lescol), lovastatin (Mevacor, Altocor, Altoprev), pitavastatin (Livalo, Pitava), pravastatin (Pravachol, Selektine, Lipostat), rosuvastatin (Crestor), and simvastatin (Zocor, Lipex); nitroglycerin; angiotensin-converting enzyme (ACE) inhibitors, such as enalapril (Vasotec®), lisinopril (Zestril®, Prinvil®), ramipril (Altace®) and captopril (Capoten®); calcium channel blockers, such as verapamil (Calan®, Isoptin®); and beta-blockers, such as carvedilol (Cored®) and metoprolol (Lopressor®, Toprol XL®).

The invention may also be used in combination with surgical or other interventional treatment regimens used for treatment of a cardiovascular disease, such as, but not limited to, use of a device, including, but not limited to, a stent, a rapamycin-coated stent, a drug-eluting stent, a bare-metal stent, a pacemaker, an implantable cardioverter-defibrillator (ICD) or a ventricular assist device (VAD).

Subjects

According to the methods of the invention, the subject or patient can be any animal that has or is diagnosed with a cardiovascular disease, such as, but not limited to, coronary artery disease. According to the methods of the invention, the subject or patient can be any animal that is predisposed to or is at risk of developing a cardiovascular disease, such as, but not limited to, coronary artery disease. In preferred embodiments, the subject is a human subject. In some embodiments, the subject is a rodent, such as a mouse. In some embodiments, the subject is a cow, pig, sheep, goat, cat, horse, dog, and/or any other species of animal used as livestock or kept as pets.

In some embodiments, the subject is already suspected to have a cardiovascular disease, such as, but not limited to, coronary artery disease. In other embodiments, the subject is being treated for a cardiovascular disease, such as, but not limited to, coronary artery disease, before being treated according to the methods of the invention. In other embodiments, the subject is not being treated for a cardiovascular disease, such as, but not limited to, coronary artery disease, before being treated according to the methods of the invention.

EXAMPLES

The following examples illustrate the present invention, and are set forth to aid in the understanding of the invention, and should not be construed to limit in any way the scope of the invention as defined in the statements of the invention which follow thereafter.

The Examples described below are provided to illustrate aspects of the present invention and are not included for the purpose of limiting the invention.

Example 1—MicroRNA-Based Strategy to Selectively Preserve Endothelial Function

The numbers in parentheses below refer to the corresponding numbered reference(s) at the end of this section.

Coronary artery disease (CAD) is a leading cause of death worldwide. Despite the benefits of drug-eluting stents (DES) concerns have been raised over their safety due to delayed endothelial cell (EC) coverage which promotes vascular restenosis and thrombosis, requiring prolonged dual anti-platelet therapy. Herein is shown a new therapeutic approach exploiting the EC specific microRNA-126 to prevent restenosis while preserving EC function.

Percutaneous coronary intervention (PCI) is one of the most commonly performed interventions that have transformed the practice of revascularization for CAD (1). However, the major drawback of this procedure is the proliferation and subsequent accumulation of vascular smooth muscle cells (VSMC), leading to restenosis (2, 3). This process, also known as intimal hyperplasia, is triggered by the injury of the arterial wall and the concurrent endothelial denudation. The advent of DES, capable of delivering an inhibitor of cell proliferation in situ has decreased, but not eliminated, the occurrence of restenosis (2, 4). The drugs that elute from the stent not only inhibit VSMC, but also EC proliferation and migration (5, 6), increasing the risk of late thrombosis, a rare and potentially catastrophic event that is caused by incomplete re-endothelization (1, 7). The ideal therapy can provide VSMC-selective anti-proliferative activity without affecting EC.

Recently, one of the crucial breakthroughs in the study of gene regulation has been the discovery of microRNAs (miRs), a class of endogenous small non-coding RNA (8, 9), miRs regulate the expression of much of the transcriptome via degradation of their target mRNA and/or inhibiting translation, miR-126 is expressed in a cell-specific manner (8,10) that enabled to selectively inhibit VSMC proliferation while preserving the capability of EC to proliferate and migrate in order to re-endothelialize the vessel. Since the expression level of miR-126 is >600-fold higher in EC than in VSMC (FIG. 2A), this miR was selected to design a VSMC-specific therapy.

Figures 2A, 2B, 2C, 2D:
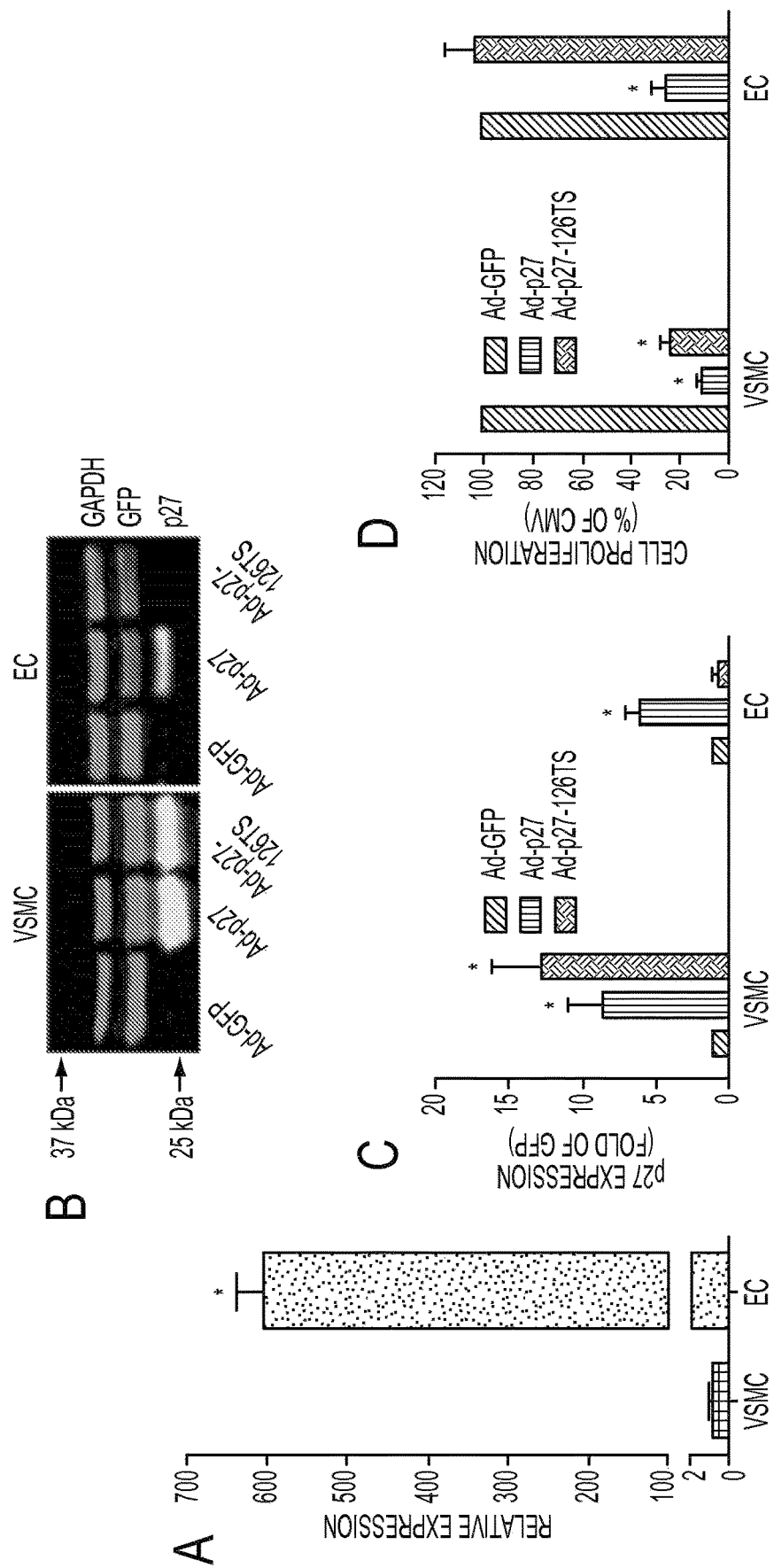
FIGS. 2A-J. Ad-p27-126TS preserves EC function in vitro.
Figures 2E, 2F, 2G, 2H:
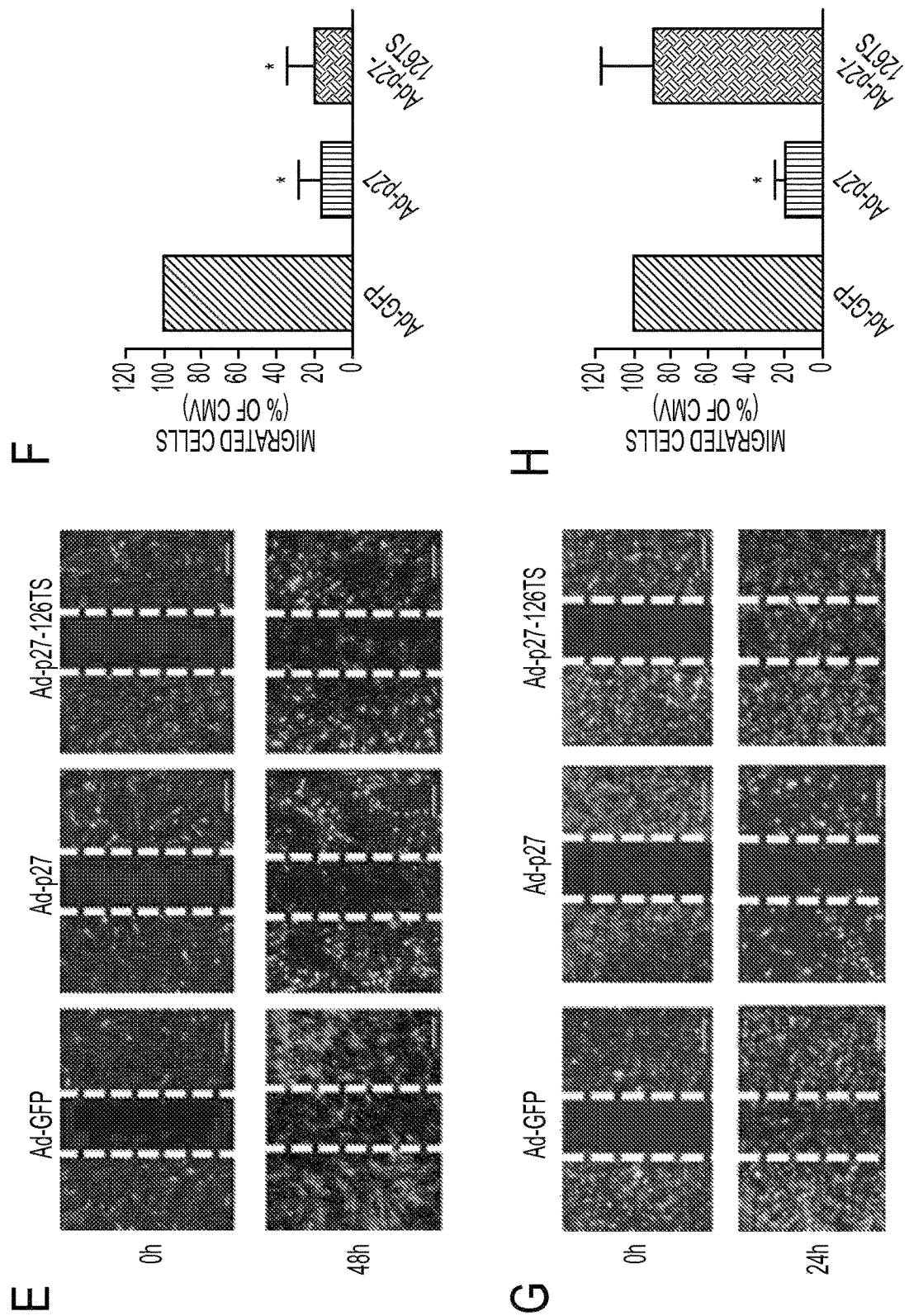
Figure 2I:
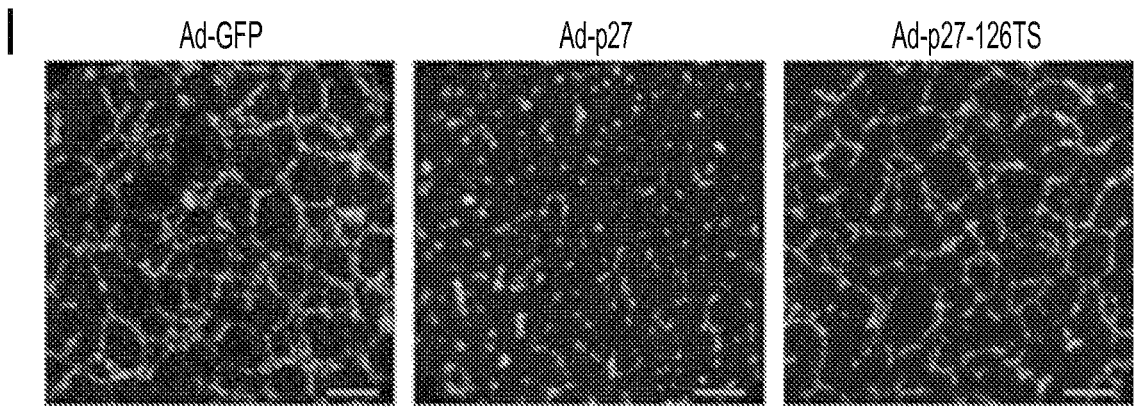
Figure 2J:
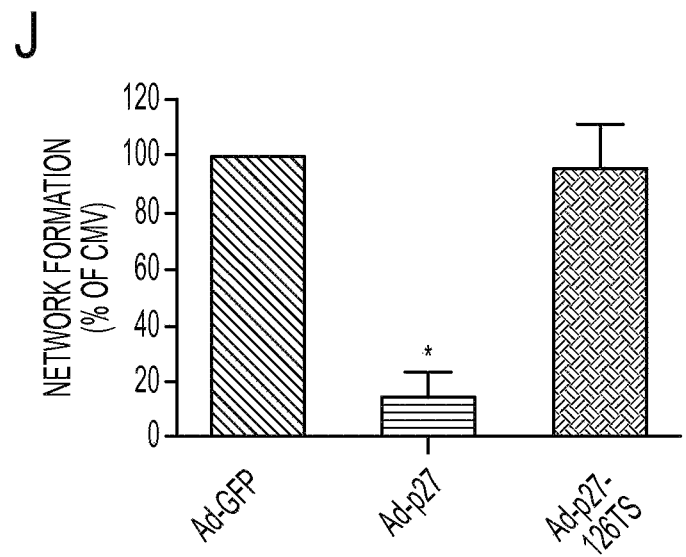
Figures 4A, 4B, 4C:
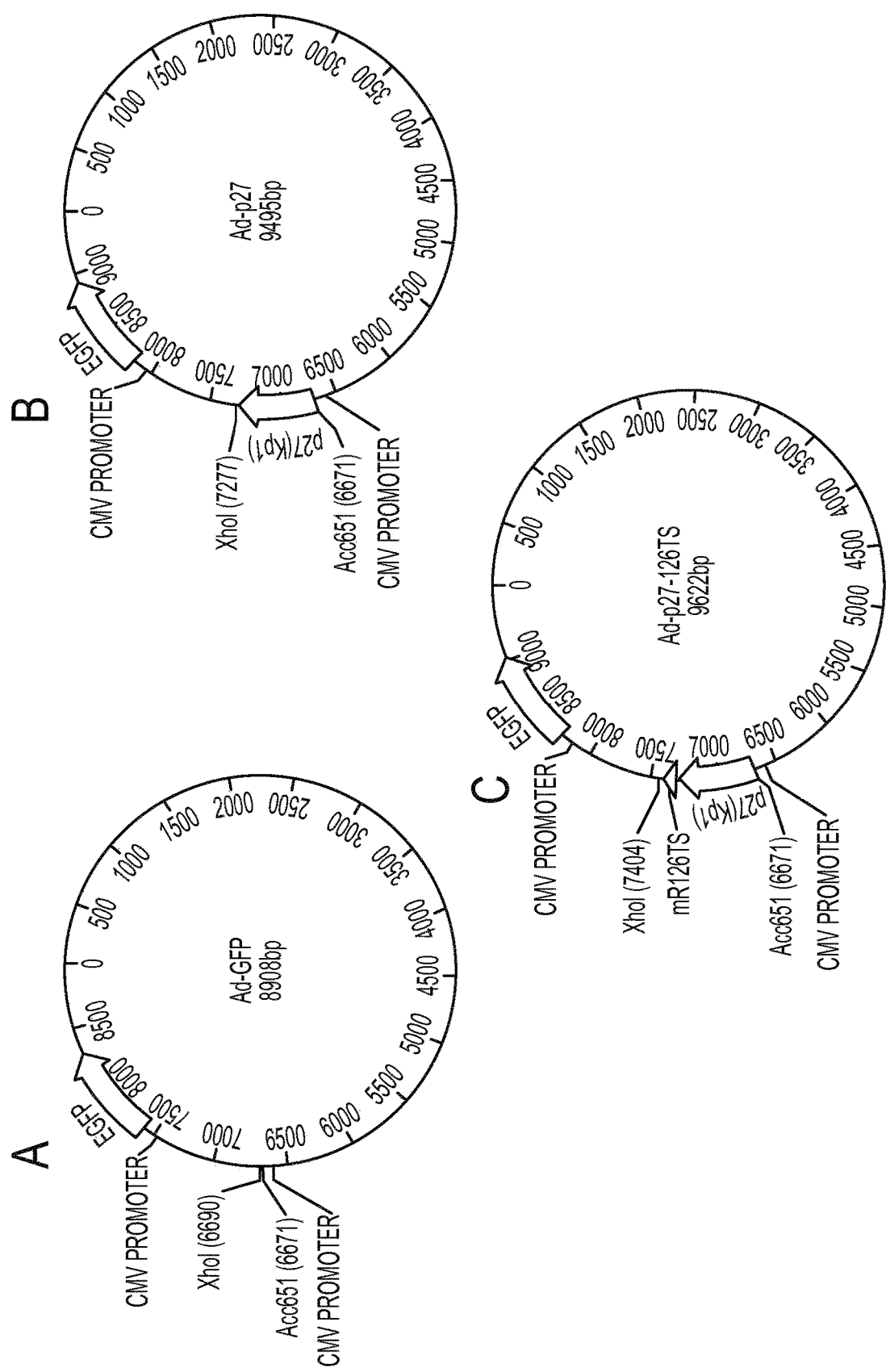
FIGS. 4A-C. Schematic representation of the used adenoviruses (Ad). A pAdTrack-CMV vector that contains a green fluorescence protein (GFP) under the control of a separate CMV promoter was used to generate three adenoviruses.

The cyclin-dependent kinase inhibitor p27$^{KIP1}$ (p27) is known to be a potent inhibitor of cell proliferation (3). Different adenoviral (Ad) vectors were designed to overexpress p27 (FIGS. 4A-C): a CMV-GFP-p27 (Ad-p27) and a CMV-GFP-p27 containing 4 target sequences of miR-126 in its 3'UTR (Ad-p27-126TS) to selectively avoid overexpression of p27 in EC. A CMV-GFP virus (Ad-GFP) was used as control. EC and VSMC were infected with these Ad and the expressions of GFP and p27 were assessed by immunoblotting (FIGS. 2B,C). p27 was not overexpressed when Ad-GFP was used in both VSMC and EC, while p27 was highly overexpressed in both cell types when Ad-p27 was used. After Ad-p27-126TS infection, p27 was overexpressed in VSMC, which do not express mir-126. Since EC do express miR-126, which binds to the four target sequences in p27-3'UTR, p27 overexpression was abolished (FIGS. 2B,C). Next, the effect of the three Ad vectors on the proliferation (FIG. 2D) and migration (FIGS. 2E-H) of EC and VSMC was tested. Ad-p27 inhibited proliferation and migration>70% in both cell types (FIGS. 2D-H). Importantly, VSMC infected with Ad-p27-126TS still showed >70% inhibition of proliferation and migration, while EC were not affected (FIGS. 2D-H). In addition, EC network formation was examined. EC infected with Ad-p27, which overexpress p27, displayed a significant decrease in the network-like formation, whereas Ad-p27-126TS infected EC formed networks comparable to Ad-GFP infected cells (FIGS. 2I,J).

Figure 5A:
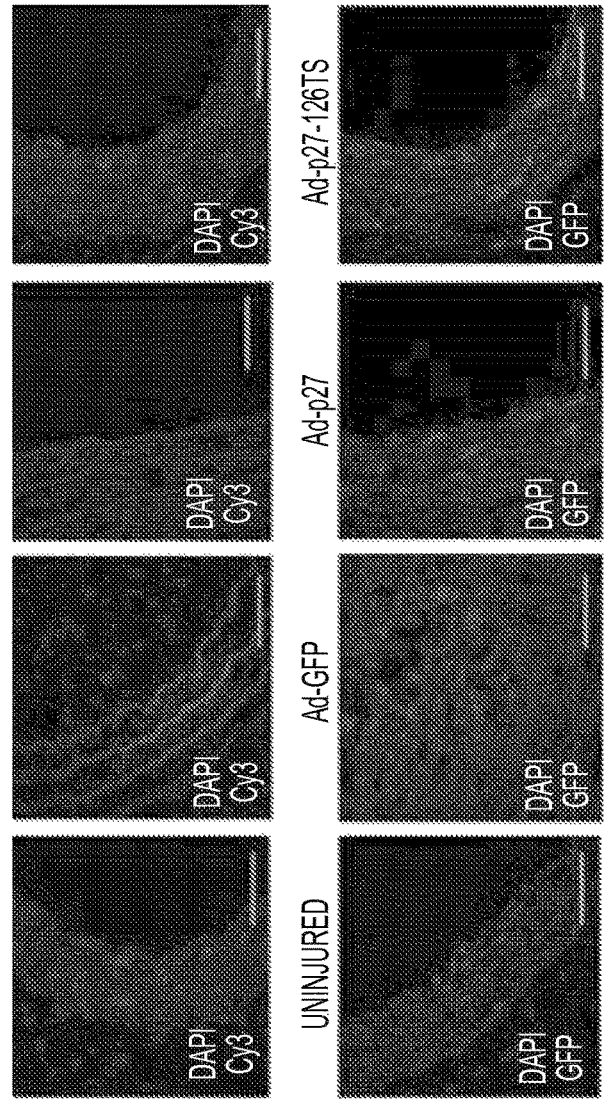
FIGS. 5A-B. Histological assessment of rat carotid arteries 2 weeks after injury and adenoviral infection.
Figure 5B:
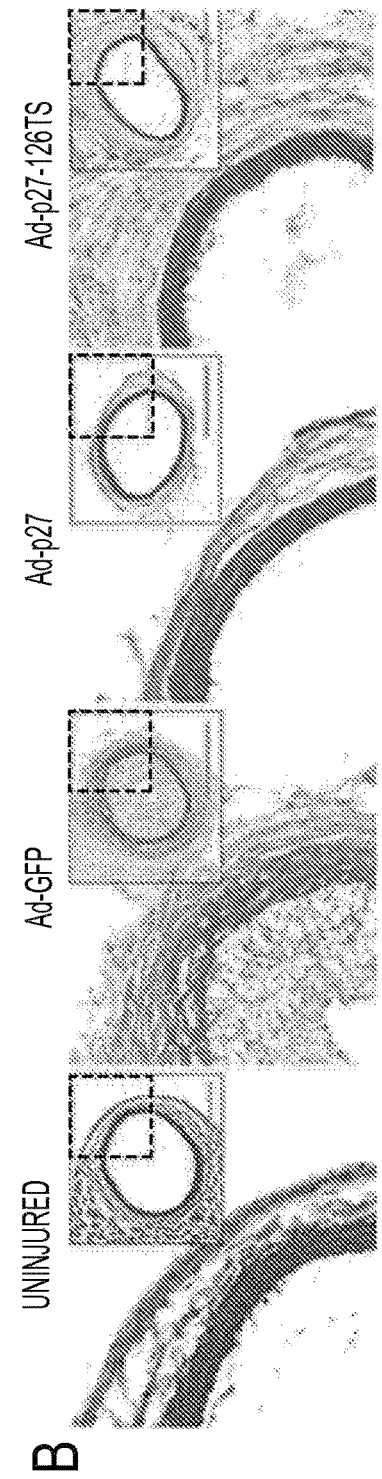

To test this approach in vivo, balloon injury of the rat carotid artery was used (11) and the injured vessel was infected with the three Ad. Two weeks after the injury, the efficiency of the infection (GFP immunostaining. FIG. 5A), the neointimal formation (FIG. 5B and FIGS. 4A,B) and the integrity of the endothelium (FIGS. 3A, C) were evaluated. Since pathological and clinical studies have reported incomplete neointimal coverage after PCI leading to thrombosis (12, 13), hypercoagulability was assessed by measuring plasma levels of D-dimer (14). The arteries infected with Ad-GFP demonstrated >2-fold increase in the neointima/media ratio after the balloon injury, and >80% decrease in re-endothelization (FIGS. 3A-C), as well as higher levels of D-dimer (FIG. 3D) compared to animals with uninjured arteries. Ad-p27 inhibited >85% of the neointimal formation and re-endothelization without affecting hypercoagulability (FIGS. 3A-D). When Ad-p27-126TS was used, the inhibition of the neointimal formation was similar to Ad-p27, widespread re-endothelization was observed, and the D-dimer level was decreased similarly to the uninjured control (FIGS. 3A-D).

Figure 3A:
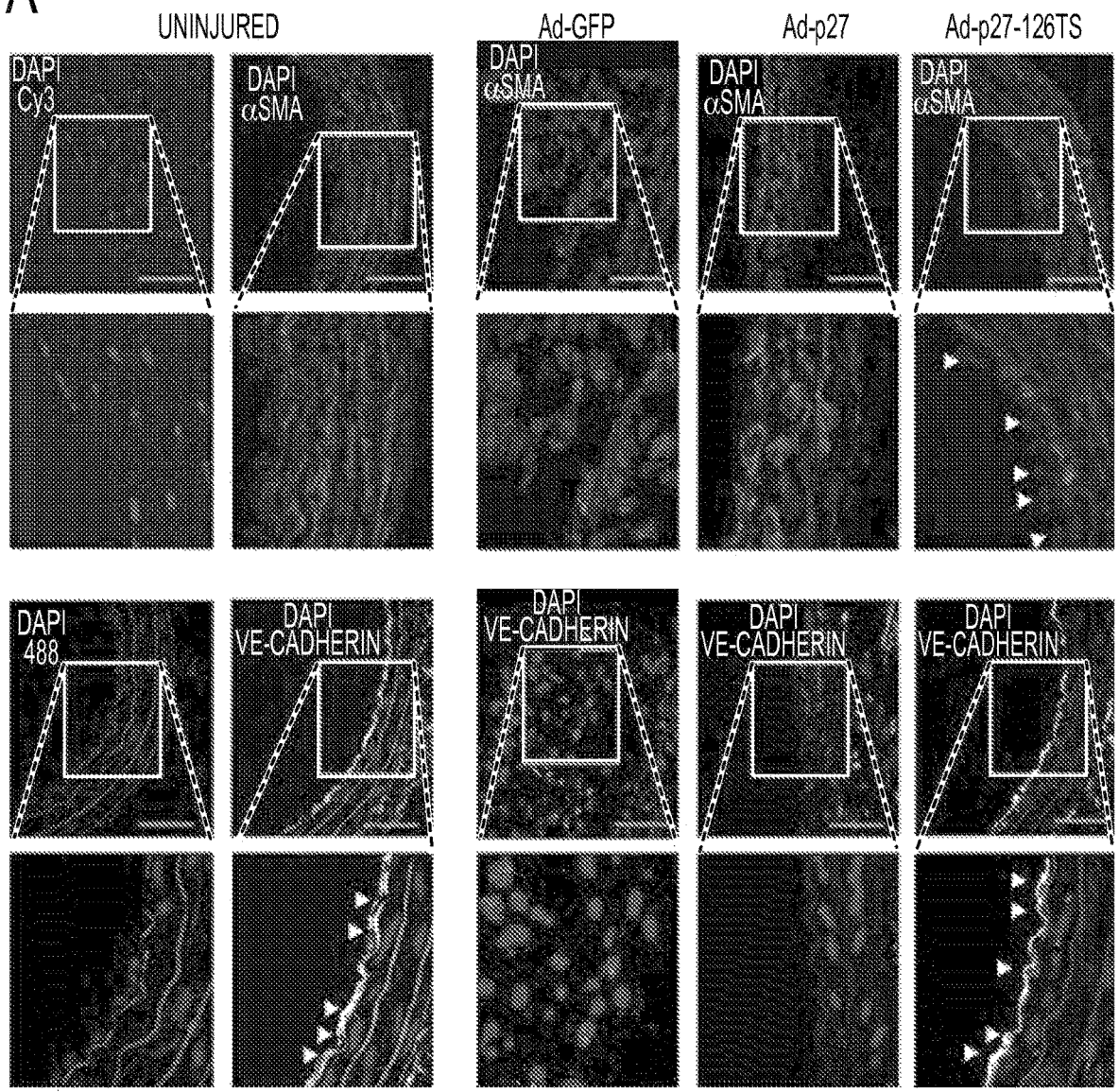
FIGS. 3A-E. Effects of Ad-p27-126TS in an in vivo model of arterial injury.
Figures 3B, 3C, 3D, 3E:
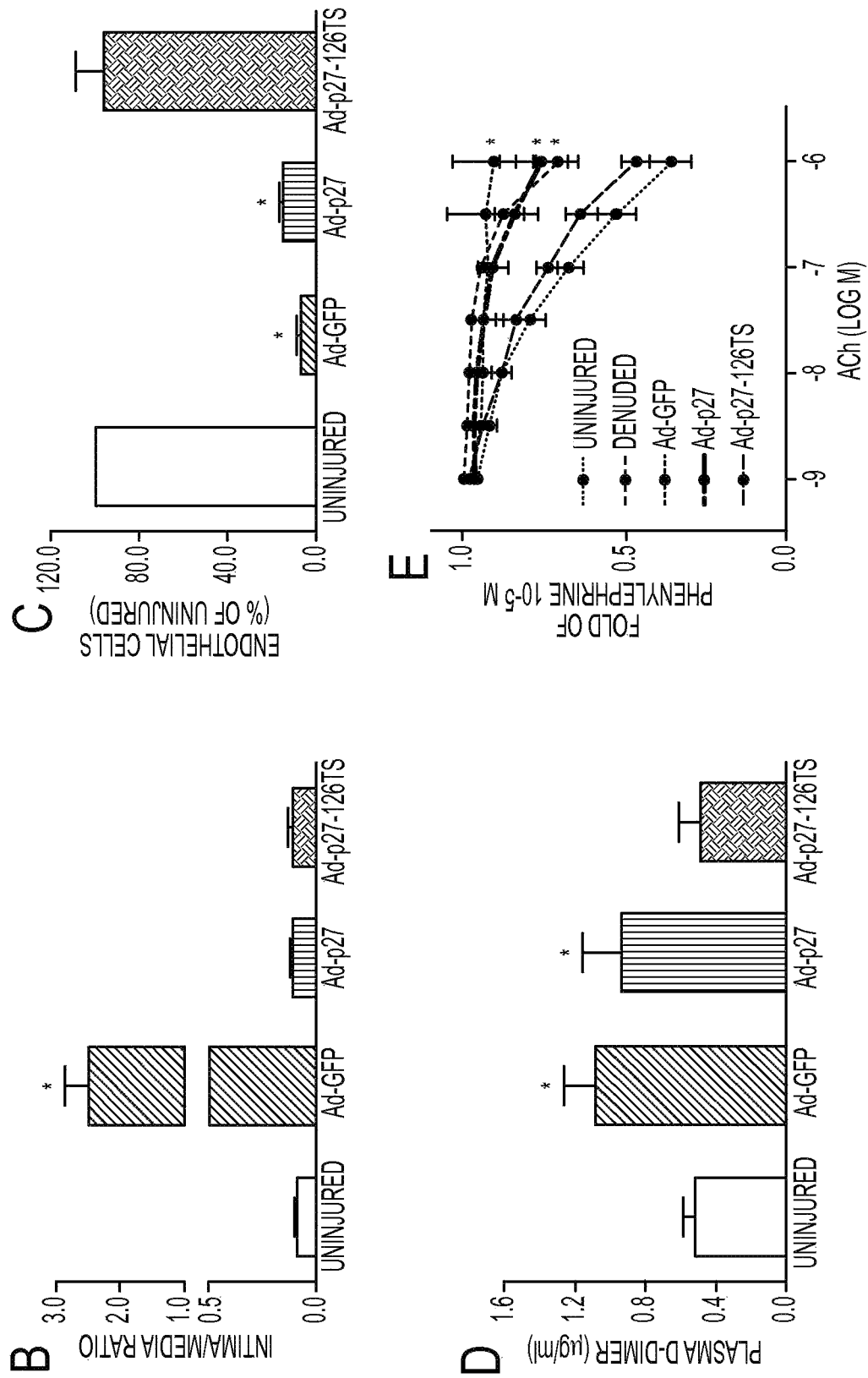

To investigate whether the new endothelium was functional, a vascular reactivity assay was performed on carotid rings harvested from rats 2 weeks after vessel surgery (15). Carotid arteries infected with Ad-GFP displayed a blunted vasodilation response to acetylcholine, most likely due to restenosis (FIG. 3E). The Ad-p27-infected vessels also showed an impaired vasodilation response, comparable to denuded control vessels. Arteries infected with Ad-p27-126TS, in contrast, showed a normal vasodilation response, comparable to uninjured control vessels (FIG. 3E).

Taken together, the data demonstrate for the first time that by exploiting the EC-specific miR-126, it is possible to specifically overexpress p27 in VSMC to inhibit proliferation and migration without affecting EC re-endothelialization. Normal endothelial function, as assessed by the reduction in D-dimer levels and acetylcholine-responsiveness, was also restored. This approach offers a basis for the development of new specific and selective therapeutic strategies to treat diverse pathological VSMC proliferative conditions, including restenosis, stent thrombosis, transplant vasculopathy, and vein graft failure. This new approach can be safer than the non-selective DES currently used in the clinical practice and can reduce the need for prolonged dual antiplatelet therapy following PCI. Further investigations can optimize the gene transfer to apply this approach in the clinical setting (8).

REFERENCES

1. Garg, S. & Serruys, P. W. *Journal of the American College of Cardiology* 56, S1-42 (2010).
2. Jukema, J. W., Verschuren, J. J. W., Ahmed, T. A. N. & Quax, P. H. *Nat. Rev. Cardiol.* 9, 53-62 (2012).
3. Marx, S. O., Totary-Jain, H. & Marks, A. R. *Circ Cardiovasc Interv* 4, 104-111 (2011).
4. Cassese, S. & Kastrati, A. *JAMA* 308, 814-815(2012).
5. Kotani, J., et al. *Journal of the American College of Cardiology* 47, 2108-2111 (2006).
6. Liu, H. T., et al. *Tex Heart Inst J* 37, 194-201(2010).
7. Wenaweser. P., et al. *Journal of the American College of Cardiology* 52, 1134-1140 (2008).
8. vanRooij, E.& Olson, E. N. *Nat Rev Drug Discov.* 11, 860-872 (2012).
9. Brown, B. D., Venneri, M. A., Zingale, A., Sergi Sergi, L. & Naldini, L. *Nat Med* 12, 585-591 (2006).
10. Wang, S., et al. *Dev Cell* 15, 261-271 (2008).
11. Iaccarino, G., Smithwick, L. A., Lefkowitz, R. J. & Koch, W. *J. Proc Natl Acad Sci USA* 96, 3945-3950 (1999).
12. Hayashi, S., et al. *The American journal of pathology* 175, 2226-2234 (2009).
13. Iakovou, I., et al. *JAMA* 293, 2126-2130 (2005).
14. Yamaguchi. K., et al. *Int J Cardiol* 153, 272-276 (2011).
15. Santulli, G., el al., *J Am Heart Assoc* 1, e001081 (2012).

Methods

The numbers in parentheses below refer to the corresponding numbered reference(s) at the end of this section.

Adenovirus Design.

Recombinant adenoviruses containing human p27 (Ad-p27) and p27 that contains four tandem targeting sequences for hsa-miR-126-3p introduced in its 3'UTR region (Ad-p27-126TS) were constructed using AdEasy XL Adenoviral Vector System (Agilent Technologies, Santa Clara, Calif.), following the manufacturer's manual. Briefly, p27 was amplified with primers 5'-agtcggtaccaccATGT-CAAACGTGCGAGTGTCTAACGG-3' (SEQ ID NO: 6) and 5'-gatctgtacaggatccTTACGTTTGACGTCTTCT-GAGGCC-3' (SEQ ID NO: 7) (start and stop codons in bold and restriction sites in lowercase) and subcloned into a carrier vector. Complementary oligonucleotides containing four targeting sequences for miR-126 (in bold) (5'attcATCG-CATTATTACTCACGGTACGAAATCCGCATTATTACT-CACGGTACGA AATCCGCATTATTACT-CACGGTACGAAATCCGCATTATTACTCACGGTACG AAT g-3' (SEQ ID NO: 8) and 5'-aattcATTCGTACCGT-GAGTAATAATGCGGATTTCGTACCGT-
GAGTAATAATGCGG ATTTCGTACCGT-
GAGTAATAATGCGGATTTCGTACCGTGAGTAATAA TGCGATg-3') (SEQ ID NO: 9) were annealed and subcloned in the 3'-UTR region of p27 with EcoRI. Next, p27 and p27-126TSx4 were amplified from the carrier vector with the following pairs of primers: 5'-agtcggtaccaccATGT-CAAACGTGCGAGTGTCTAACGG-3' (SEQ ID NO: 6) as a sense primer for both constructs, and 5'-agtcctcgagT-TACGTTTGACGTCTTCTGAGGCC-3' (SEQ ID NO: 10) and 5'-agtcctcgagaTTCGTACCGTGAGTAATAATGCG-GATTTC-3' (SEQ ID NO: 11) as antisense primers for p27 and p27-126TSx4, respectively. The resulting PCR products were subcloned into pAdTrack-CMV shuttle vector (using Acc65 I and Xho I restriction sites in lowercase) under the control of a cytomegalovirus (CMV) promoter. All the constructs also contain a green fluorescence protein (GFP) under the control of a separate CMV promoter. All final virus constructs were purified by ultracentrifugation in CsCl gradient, dialyzed, confirmed by sequencing and titrated in HEK cells.

Cell Culture.

Human umbilical venous endothelial cells (HUVEC) were cultured in EGM2 Bullet Kit medium (Lonza, Basel, Switzerland) on dishes coated with type 1 rat tail collagen (VWR, Radnor, Pa.). Human umbilical vascular smooth muscle cells (VSMC) and SmGM-2 Bullet Kit medium were purchased from Lonza. The cells in all assays were below passage 6 and cultured at a density that allowed cell division throughout the course of the experiment.

Quantitative Real Time-PCR.

TaqMan® microRNA Assays (Life Technologies) were used to quantify mature miRNAs. cDNA was synthesized by priming with miRNA-specific looped primers, or U1 8 as endogenous control. Total RNA (100 ng) extracted with miRNeasy Mini Kit (Quiagen, Germantown, Md.) was used for each reverse transcription reaction according to the manufacturer's specifications and incubated for 30 min at 16° C., 30 min at 42° C., and 5 min at 85° C. and stored at 4° C. PCR was performed using 4.5 ng cDNA, lx TaqMan® Universal PCR Master Mix (P/N: 4324018) and TaqMan® MicroRNA assay. All reactions, excluding no-template controls and non-reverse-transcribed controls were run in triplicate, incubated in 96-well plates at 95° C. for 20 seconds, followed by 40 cycles of 95° C. for 3 seconds and 60° C. for 30 seconds using the ABI 7500 Fast Real Time PCR Detection System. Real-time PCR data were analyzed using the comparative CT method, normalizing against the expression of U18.

Proliferation, Migration, and Network Formation Assays.

VSMC and EC were infected with 20 or 30 pfu/cell, respectively. Proliferation assay was carried out six days after infection by using the Cell-Proliferation-Reagent kit (Roche, Basel, Switzerland) according to the manufacturer's instruction. The absorbance was measured at 450 nm (with 690 nm reference wavelength) using Infinite® F500 microplate reader (Tecan, Mannedorf, Switzerland). Cellular migration was assessed as previously described (1). The formation of network-like structures assay was performed and quantified as previously described and validated (1, 2). Several fields of view were captured per well and experiments were repeated three times by blinded observers.

Immunoblotting.

Immunoblot analysis was performed as previously described (3). Briefly, samples were resolved by SDS-PAGE and proteins transferred to poly-vinylidene difluoride and visualized by immunoblotting using infrared-labeled anti-rabbit (red) and anti mouse (green) secondary antibodies (1:10,000, LI-COR Biosciences. Lincoln, Nebr.). Band intensities were quantified with the Odyssey Infrared Imaging System (LI-COR Biosciences). Blots were probed with the following antibodies: rabbit anti-GAPDH (Cell signaling Technology®), rabbit anti-GFP (Life Technologies) and mouse anti-p27 (BD Transduction Laboratories™), San Jose, Calif.). Data are presented as arbitrary units after normalization for GAPDH as loading control.

In Vivo Balloon Injury.

The animals were housed in a 22° C. room with a 12-hour light/dark cycle. Balloon injury of the right carotid artery was performed in male Sprague Dawley rats (weighing 300±30 g, Harlan, South Easton, Mass.) using a Hyper-Glide™ ballon catheter (Micro Therapeutics, Inc. Irvine, Calif.), partially modifying a previously described procedure (4). Briefly, the animals were anesthetized by isoflurane (4%) inhalation and maintained by mask ventilation (isoflurane 2%), and the right common, external and internal carotid arteries were exposed and isolated. Through the external carotid, the balloon catheter was introduced in the common carotid and inflated 7 times. After injury, the common carotid artery was flushed twice with PBS, and a solution of PBS and adenovirus [$5 \times 10^9$ plaque-forming unit (pfu)/100 μI] was injected and allowed to incubate in the common carotid in the absence of flow for 20 min. During this procedure the tension of common carotid artery was maintained by placing microvascular clips (Harvard Apparatus, Holliston, Mass.) on the internal and the common carotids (5). The adenovirus then was removed, the external carotid was tied and the blood flow was restored through the common and the internal carotid arteries. Following wound closure, the rats were given ad libitum access to food and water. All experiments were performed by blinded investigators.

D-Dimer Measurement.

Hypercoagulability was assessed measuring plasma levels of D-dimer (6) using a rat immunoassay (USCN Life Science Inc. Houston, Tex.) in accordance to the manufacturer's instructions.

Morphological Analysis.

Two weeks after surgery, the rats were euthanized and the carotid arteries were fixed by perfusion at 100 mmHg with 100 ml of PBS, followed by 80 ml of PBS containing 4% paraformaldehyde via a cannula placed in the left ventricle. Both right and left common carotid arteries were then excised, cut in two portions and embedded in optimal cutting temperature (OCT) medium (Sakura Finetek, Tokyo, Japan) for cryosectioning. Subsequently, 10 μm sections were cut every 20 μm and submitted in toto for histological evaluation. Sections were processed for staining with anti-α-smooth muscle actin (α-SMA, Sigma-Aldrich, 1:1000 for 3 hat room temperature), anti VE cadherin (Abeam, Cambridge, Mass., 1:100 overnight at 4° C.) specific for EC (7), anti GFP (Life Technologies, 1:1000 overnight at 4° C.) antibodies. Fluorescent-labeled secondary antibodies (1:1000) were incubated at room temperature for 1 hour. Samples were then washed with PBS and mounted with SlowFade® Gold antifade reagent with DAPI (Life Technologies). Images were taken by using a Nikon Al scanning confocal microscope (Nikon Instruments, Melville, N.Y.) and acquired with NIS-Elements advanced research software. Images were optimized for contrast, without any further manipulation. Neointima/media ratios were calculated using a computerized image analysis system (Image J), as previously described (4).

Vascular Reactivity.

After isolation from the rats, common carotid arteries were suspended in isolated tissue baths filled with 25 mL Krebs-Henseleit solution (in mMol/L: NaCl 118.3, KCl 4.7, $CaCl_2$ 2.5, $MgSO_4$ 1.2, $KH_2PO_4$ 1.2, $NaHCO_3$ 25, and glucose 5.6) continuously bubbled with a mixture of 5% $CO_2$ and 95% $O_2$ (pH 7.38 to 7.42) at 37°=C. as previously described (8). Endothelium-dependent vasorelaxation was assessed in vessels pre-constricted with phenylephrine ($10^{-5}$ M) in response to acetylcholine from $10^{-9}$ to $10^{-6}$ M, freshly prepared on the day of experiment (5, 9). Concentrations are reported as the final molar value in the organ bath. Endothelium-independent vasodilatation was tested after mechanical endothelium removal of the endothelial layer.

REFERENCES

1. Ciccarelli, M., et al. Endothelial alpha1-adrenoceptors regulate neo-angiogenesis. *Br J Pharmacol* 153, 936-946 (2008).
2. Santulli, G., et al. Evaluation of the anti-angiogenic properties of the new selective alpha Vbeta3 integrin antagonist RGDechiHCit. *J Transl Med* 9, 7 (2011).
3. Totary-Jain, H., et al. Rapamycin resistance is linked to defective regulation of Skp2. *Cancer Res* 72, 1836-1843 (2012).
4. Iaccarino, G., Smithwick, L. A., Lefkowitz, R. J. & Koch, W. J. Targeting Gbeta gamma signaling in arterial vascular smooth muscle proliferation: a novel strategy to limit restenosis. *Proc Natl Acad Sci USA* 96, 3945-3950 (1999).
5. Iaccarino, G., et al. AKT participates in endothelial dysfunction in hypertension. *Circulation* 109, 2587-2593 (2004).
6. Yamaguchi, K., et al. Local persistent hypercoagulability after sirolimus-eluting stent implantation in patients with stable angina. *Int J Cardiol* 153, 272-276 (2011).
7. Vestweber, D. VE-cadherin: the major endothelial adhesion molecule controlling cellular junctions and blood vessel formation. *Arterioscler Thromb Vasc Biol* 28, 223-232 (2008).
8. Santulli. G., et al. In vivo properties of the proangiogenic peptide QK. *J Transl Med* 7, 41 (2009).
9. Santulli, G., et al. CaMK4 Gene Deletion Induces Hypertension. *J Am Heart Assoc* 1, e001081 (2012).

Example 2

Coronary artery disease is currently a leading cause of death worldwide. Despite all the benefits of drug-eluting stents (DES), concerns have been raised over their long-term safety, with particular reference to stent thrombosis due to delayed endothelial cell (EC) coverage. Described herein is a method that exploits the endogenous miRNAs to specifically inhibit vascular smooth muscle cell (VSMC) proliferation, the major cause of restenosis, without affecting reendothelialization.

By inserting four target sequences of the EC specific mir-126 into the 3'UTR of p27 expressing adenoviruses (p27-126TS), VSMC proliferation and migration was specifically inhibited, while EC were able to proliferate, migrate and form capillary-like networks. Balloon injured rat carotid artery infected with p27-126TS viruses exhibited complete inhibition of restenosis with complete re-endothelialization after two weeks (FIG. 3B). Moreover, hypercoagulability assessed by measuring plasma levels of D-dimer in the serum of rats treated with the p27-126TS was similar to the non-injured control (FIG. 3D). Finally, the vasodilatative response to acetylcholine of balloon injured carotid arteries treated with p27-126TS adenovirus were comparable to those of the control-noninjured vessel (FIG. 3E). The data above can lead to a safer therapy than the non-selective DES and can diminish the need for prolonged dual antiplatelet therapy following percutaneous coronary intervention.

Example 3

Antithrombotic and/or antiinflammatory genes will be incorporated into the adenovirus expression vectors described in the examples above, or into any other DNA delivery system, as described in the Detailed Description. Such genes will be incorporated into the adenovirus vectors under the control of a second CMV promoter.

Example antithrombotic and/or antiinflammatory genes include the following:

Ectonucleoside triphosphate diphosphohydrolase, ENTPD1. The nucleic acid sequence of the gene encoding ENTPD1, including, but not limited to, the nucleic acid sequence of the open reading frame of the gene, is known in the art. The nucleic acid sequence of the gene encoding human ENTPD1, including, but not limited to, the nucleic acid sequence of the open reading frame of the human gene, is known in the art. The amino acid sequences of the ENTPD1 polypeptide and protein, including, but not limited to, the amino acid sequences of the human ENTPD1 polypeptide and proteins, are known in the art. The GenBank accession number of a polypeptide sequence of human ENTPD1 1s AAH47664.

Prostacyclin synthase, PTGIS. The nucleic acid sequence of the gene encoding PTGIS, including, but not limited to, the nucleic acid sequence of the open reading frame of the gene, is known in the art. The nucleic acid sequence of the gene encoding human PTGIS, including, but not limited to, the nucleic acid sequence of the open reading frame of the human gene, is known in the art. The amino acid sequences of the PTGIS polypeptide and protein, including, but not limited to, the amino acid sequences of the human PTGIS polypeptide and proteins, are known in the art. The Gen-Bank accession number of a polypeptide sequence of human PTGIS is BAA11910.

Tissue factor pathway inhibitor, TFPI. The nucleic acid sequence of the gene encoding TFPI, including, but not limited to, the nucleic acid sequence of the open reading frame of the gene, is known in the art. The nucleic acid sequence of the gene encoding human TFPI, including, but not limited to, the nucleic acid sequence of the open reading frame of the human gene, is known in the art. The amino acid sequences of the TFPI polypeptide and protein, including, but not limited to, the amino acid sequences of the human TFPI polypeptide and proteins, are known in the art. The GenBank accession number of the nucleic acid sequence of human TFPI is AF021834.

What is claimed is:

1. A pharmaceutical composition for inhibiting restenosis in a subject, the composition comprising: a vector comprising a p27 gene and a miR-126 target sequence within the 3'UTR region of the p27 gene; a physiologically compatible buffer, and a pharmaceutically acceptable carrier or excipient; wherein the composition inhibits restenosis when applied to the subject's vasculature, wherein the composition is applied to a drug-eluting stent.

2. The pharmaceutical composition of claim 1, wherein the miR-126 target sequence is represented by SEQ ID NO:2.

3. The pharmaceutical composition of claim 1, wherein the vector comprises a second gene-of-interest.

4. The pharmaceutical composition of claim 3, wherein the second gene-of-interest comprises at least one miRNA target sequence within the 3'UTR region the second gene-of-interest.

5. The pharmaceutical composition of claim 1, wherein the nucleic acid vector is at least one of a plasmid, a viral vector, a cosmid, an artificial chromosome, or a nanoparticle.

6. The pharmaceutical composition of claim 5, wherein the viral vector is an adenoviral vector, an Adeno-associated viral vector, or a lentivirus vector.

7. The pharmaceutical composition of claim 1, wherein inhibiting restenosis comprises inhibiting vascular smooth muscle cell (VSMC) proliferation, migration, or neointimal formation without affecting endothelial cell function.

8. The pharmaceutical composition of claim 1, wherein the vector is present in the composition in an amount of at least about $1 \times 10^9$ pfu/100 µl.

9. The pharmaceutical composition of claim 1, wherein the physiologically compatible buffer is Hank's solution, Ringer's solution, or Phosphate buffered saline (PBS).

10. The pharmaceutical composition of claim 1, wherein the pharmaceutically acceptable carrier or excipient comprises one or more of dispersion media, coatings, antibacterial and antifungal agents, and isotonic and absorption delaying agents.

11. The pharmaceutical composition of claim 1, wherein the pharmaceutically acceptable carrier or excipient comprises one or more of glycols, oils, alcohols, aqueous solvents, organic solvents, DMSO, saline solutions, physiological buffer solutions, peptide carriers, starches, sugars, preservatives, antioxidants, coloring agents, pH buffering agents, granulating agents, lubricants, binders, disintegrating agents, emulsifiers, binders, excipients, extenders, glidants, solubilizers, stabilizers, surface active agents, suspending agents, tonicity agents, viscosity-altering agents, carboxymethyl cellulose, crystalline cellulose, glycerin, gum arabic, lactose, magnesium stearate, methyl cellulose, powders, saline, sodium alginate, and pluronic gel.

12. The pharmaceutical composition of claim 1, wherein the composition further comprises one or more of aspirin, a statin, atorvastatin, fluvastatin, lovastatin, pitavastatin, pravastatin, rosuvastatin, simvastatin, nitroglycerin, an angiotensin-converting enzyme (ACE) inhibitor, enalapril, lisinopril, ramipril, captopril, a calcium channel blocker, verapamil, a betablocker, carvedilol, and metoprolol.

13. A method of inhibiting restenosis in a subject, the method comprising:
administering to the subject's vasculature an effective amount of the pharmaceutical composition of claim 1.

14. The method of claim 13, wherein inhibiting restenosis comprises inhibiting vascular smooth muscle cell (VSMC) proliferation, migration, or neointimal formation without affecting endothelial cell function.

15. The method of claim 13, wherein the vector is present in the composition in an amount of at least about $1 \times 10^9$ pfu/100 µl.

* * * * *

SEQUENCE LISTING

<160> NUMBER OF SEQ ID NOS: 11

<210> SEQ ID NO 1
<211> LENGTH: 22
<212> TYPE: RNA
<213> ORGANISM: Homo sapiens

<400> SEQUENCE: 1
ucguaccgug aguaauaaug cg                                                22

<210> SEQ ID NO 2
<211> LENGTH: 22
<212> TYPE: DNA
<213> ORGANISM: Homo sapiens

<400> SEQUENCE: 2
cgcattatta ctcacggtac ga                                                22

<210> SEQ ID NO 3
<211> LENGTH: 198
<212> TYPE: PRT
<213> ORGANISM: Homo sapiens

<400> SEQUENCE: 3

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 4
<211> LENGTH: 2413
<212> TYPE: DNA
<213> ORGANISM: Homo sapiens

<400> SEQUENCE: 4
cttcttcgtc agcctcccctt ccaccgccat attgggccac taaaaaaagg gggctcgtct      60
tttcggggtg tttttctccc cctccccctgt ccccgcttgc tcacggctct gcgactccga     120
cgccggcaag gtttggagag cggctggggtt cgcgggaccc gcgggcttgc acccgcccag     180
actcggacgg gctttgccac cctctccgct tgcctggtcc cctctcctct ccgccctccc     240
gctcgccagt ccatttgatc agcggagact cggcggccgg gcggggcctt ccccgcagcc     300
cctgcgcgct cctagagctc gggccgtggc tcgtcggggt ctgtgtcttt tggctccgag     360

```
ggcagtcgct gggcttccga gaggggttcg ggctgcgtag gggcgctttg ttttgttcgg      420
ttttgttttt ttgagagtgc gagagaggcg gtcgtgcaga cccgggagaa agatgtcaaa      480
cgtgcgagtg tctaacggga gccctagcct ggagcggatg gacgccaggc aggcggagca      540
ccccaagccc tcggcctgca ggaacctctt cggcccggtg gaccacgaag agttaacccg      600
ggacttggag aagcactgca gagacatgga agaggcgagc cagcgcaagt ggaatttcga      660
ttttcagaat cacaaacccc tagagggcaa gtacgagtgg caagaggtgg agaagggcag      720
cttgcccgag ttctactaca gaccccgcg gcccccaaa ggtgcctgca aggtgccggc       780
gcaggagagc caggatgtca gcgggagccg cccggcggcg cctttaattg gggctccggc      840
taactctgag gacacgcatt tggtggaccc aaagactgat ccgtcggaca gccagacggg      900
gttagcggag caatgcgcag gaataaggaa gcgacctgca accgacgatt cttctactca      960
aaacaaaaga gccaacagaa cagaagaaaa tgtttcagac ggttccccaa atgccggttc      1020
tgtggagcag acgcccaaga agcctggcct cagaagacgt caaacgtaaa cagctcgaat      1080
taagaatatg tttccttgtt tatcagatac atcactgctt gatgaagcaa ggaagatata      1140
catgaaaatt ttaaaaatac atatcgctga cttcatggaa tggacatcct gtataagcac      1200
tgaaaaacaa caacacaata acactaaaat tttaggcact cttaaatgat ctgcctctaa      1260
aagcgttgga tgtagcatta tgcaattagg ttttttcctta tttgcttcat tgtactacct      1320
gtgtatatag ttttaccttt ttatgtagca cataaacttt ggggaaggga gggcagggtg      1380
gggctgagga actgacgtgg agcggggtat gaagagcttg ctttgattta cagcaagtag      1440
ataaatattt gacttgcatg aagagaagca attttgggga aggggtttgaa ttgttttctt      1500
taaagatgta atgtcccttt cagagacagc tgatacttca tttaaaaaaa tcacaaaaat      1560
ttgaacactg gctaaagata attgctattt attttttacaa gaagtttatt ctcatttggg      1620
agatctggtg atctcccaag ctatctaaag tttgttagat agctgcatgt ggcttttttta     1680
aaaaagcaac agaaacctat cctcactgcc ctccccagtc tctcttaaag ttggaattta      1740
ccagttaatt actcagcaga atggtgatca ctccaggtag tttggggcaa aaatccgagg      1800
tgcttgggag ttttgaatgt taagaattga ccatctgctt ttattaaatt tgttgacaaa      1860
attttctcat tttctttttca cttcgggctg tgtaaacaca gtcaaaataa ttctaaatcc      1920
ctcgatattt ttaaagatct gtaagtaact tcacattaaa aaatgaaata tttttttaatt      1980
taaagcttac tctgtccatt tatccacagg aaagtgttat ttttcaagga aggttcatgt      2040
agagaaaagc acacttgtag gataagtgaa atggatacta catctttaaa cagtatttca      2100
ttgcctgtgt atggaaaaac catttgaagt gtacctgtgt ataactct gtaaaaacac        2160
tgaaaaatta tactaactta tttatgttaa aagattttt ttaatctaga caatatacaa       2220
gccaaagtgg catgttttgt gcatttgtaa atgctgtgtt gggtagaata ggttttcccc      2280
tcttttgtta aataatatgg ctatgcttaa aaggttgcat actgagccaa gtataatttt      2340
ttgtaatgtg tgaaaaagat gccaattatt gttacacatt aagtaatcaa taaagaaaac      2400
ttccatagct att                                                         2413
```

<210> SEQ ID NO 5  
<211> LENGTH: 6  
<212> TYPE: PRT  
<213> ORGANISM: Artificial Sequence  
<220> FEATURE:  
<223> OTHER INFORMATION: Description of Artificial Sequence: Synthetic 6xHis tag

<400> SEQUENCE: 5

His His His His His His
1               5

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtcggtacc accatgtcaa acgtgcgagt gtctaacgg                              39

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatctgtaca ggatccttac gtttgacgtc ttctgaggcc                             40

<210> SEQ ID NO 8
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
aattcatcgc attattactc acggtacgaa atccgcatta ttactcacgg tacgaaatcc      60
gcattattac tcacggtacg aaatccgcat tattactcac ggtacgaatg                 110

<210> SEQ ID NO 9
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
aattcattcg taccgtgagt aataatgcgg atttcgtacc gtgagtaata atgcggattt      60
cgtaccgtga gtaataatgc ggatttcgta ccgtgagtaa taatgcgatg                 110

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtcctcgag ttacgtttga cgtcttctga ggcc                                  34

<210> SEQ ID NO 11
<211> LENGTH: 40
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 11
agtcctcgag attcgtaccg tgagtaataa tgcggatttc                                40
```